(12) United States Patent
Klinken et al.

(10) Patent No.: US 8,148,343 B2
(45) Date of Patent: Apr. 3, 2012

(54) TUMOR SUPPRESSOR FACTOR

(75) Inventors: Svend Peter Klinken, Mosman Park (AU); Jean-Philippe Lalonde, Subiaco (AU); James Howard Williams, Kensington (AU)

(73) Assignee: Molecular Discovery Systems, North Perth (AU)

( * ) Notice: Subject to any disclaimer, the term of this patent is extended or adjusted under 35 U.S.C. 154(b) by 264 days.

(21) Appl. No.: 12/356,909

(22) Filed: Jan. 21, 2009

(65) Prior Publication Data

US 2010/0239649 A1    Sep. 23, 2010

Related U.S. Application Data

(63) Continuation of application No. 10/130,971, filed as application No. PCT/AU00/01439 on Nov. 24, 2000, now Pat. No. 7,560,253.

(30) Foreign Application Priority Data

Nov. 24, 1999  (AU) ...................................... PQ4216

(51) Int. Cl.
    *A61K 48/00*    (2006.01)
(52) U.S. Cl. .................. 514/44 R; 536/23.1; 435/320.1
(58) Field of Classification Search .................. None
    See application file for complete search history.

(56) References Cited

U.S. PATENT DOCUMENTS

| 5,670,314 A | 9/1997 | Christman et al. |
| 6,033,857 A * | 3/2000 | Tavtigian et al. .................. 435/6 |
| 2002/0052308 A1 | 5/2002 | Rosen et al. |

FOREIGN PATENT DOCUMENTS

| WO | 91/17171 | 11/1991 |
| WO | 99/38972 | 5/1999 |

OTHER PUBLICATIONS

Vinyals et al, Gene Ther 1999;6:22-33.*
Lane, Trends Mole Ther 2002;8:S38-42.*
Verma et al, Nat. 1997; 389:239-242.*
Makrides et al. Protein Exp Pur. 1999; 17:183-202.*
McCluskie et al. Mol Med May 1999;5:287-300.*
Anderson, Hum Gene Ther 2002;13:1261-2.*
Written Opinion for International Application No. PCT/AU00/01439, mailed Jul. 13, 2001 (6 pages).
International Search Report for International Application No. PCT/AU00/01439, mailed Feb. 9, 2001 (3 pages).
International Preliminary Examination Report for International Application No. PCT/AU00/01439, mailed Jul. 13, 2001 (6 pages).
Supplementary Partial European Search Report for European Patent Application No. EP 00 977 327.6, dated May 7, 2004 (2 pages).
European Examination Report for European Application No. EP 00 977 327.6, dated Aug. 17, 2006 (3 pages).
Database Fasta (Online) Aug. 4, 1999 Kikuno et al. Prediction of the coding sequences of unidentified human genes. XIV. The complete sequences of 100 new CDNA clones from brain which codes for large proteins in vitro. Retrieved from EMBL Database accession No. AB029021 XP002274849.
Database Fasta (Online) May 1, 2000 Kikuno et al. Prediction of the coding sequences of unidentified human genes. XIV. The complete sequences of 100 new CDNA clones from brain which codes for large proteins in vitro. Retrieved from EMBL Database accession No. Q9UPQ4 XP002274850.
Kikuno et al., Prediction of the coding sequences of unidentified human genes XIV. The complete sequences of 100 new DNA Clones from brain which code for large proteins in vitro, *DNA Res.*, vol. 6, No. 3, Jun. 3, 1999, pp. 197-205.
Williams JH et al., HLS7, a hemopoietic linkage switch gene homologous to the leukemia inducing gene MLF, *EMBO Journal*, vol. 18, No. 20, 1999 pp. 5559-5568.
Klinken et al., Hemopoietic linkage switch: v-raf oncogene coverts Emu-myc transgenic B cells into macrophages, *Cell*, vol. 53, Jun. 7, 1988, pp. 857-867.

* cited by examiner

*Primary Examiner* — Q. Janice Li
(74) *Attorney, Agent, or Firm* — K&L Gates LLP

(57) ABSTRACT

The present invention relates to a tumor suppressor gene, termed HLS-5 and the amino acid sequence that it encodes. The present invention also relates to the use of HLS-5 in regulating cell growth.

13 Claims, 14 Drawing Sheets

| | HOMOLOGY | EXPRESSION (mRNA) | |
|---|---|---|---|
| | | J2E | J2E-m2 |
| HLS1 | Cyclooxygenase 2 | − | + |
| HLS2 | No homology | − | + |
| HLS3 | Mitochondrial DNA | nd | nd |
| HLS4 | Reg. subunit PKC | nd | nd |
| HLS5 | RBCC | − | + |
| HLS6 | GDP dissociation inhibitor D4 | − | + |
| HLS7 | Myeloid Leukemia Factor-1 | − | + |
| HLS8 | HLS 1 + 2 concatamer | nd | |

Figure 2

SEQUENCE LISTING

<160> NUMBER OF SEQ ID NOS: 16

<210> SEQ ID NO 1
<211> LENGTH: 3648
<212> TYPE: DNA
<213> ORGANISM: Mus musculus

<400> SEQUENCE: 1

```
cgtactttt  gcccgcaggc  taggcatgaa  ggcggcgaca  ccggtggtgg  tgacggcggc       60
tgctcctgcg  atggagccgg  gcccttctgt  gtccccgggg  ccttcgcgct  ccttcaaaga      120
ggagctgctg  tgtgccgtgt  gctacgaccc  gttccgcgac  gcagtaactc  tgcgctgtgg      180
ccacaacttc  tgccgccggt  gcgtgagcgg  ctgctgggag  gtgcagacga  cgccctcgtg      240
tccggtgtgc  aaggaacgag  cggtgcccgg  ggagctgcgc  accaaccaca  cgctcaacaa      300
cctggtggag  accttgctgc  gcgaggaggc  tgagggcgcg  cgctggaccg  gtcgccggtc      360
cccgcgcccc  tgccgtgcgc  accgtgcccc  gctcacgctc  ttctgcctgg  aggacaagga      420
gctgctgtgc  tgtgcttgcc  aggccgacgc  ccggcaccaa  gagcatcgtg  tgcagcccat      480
caaggacact  gcgcaagact  tccgggccaa  gtgtaagaac  atggagcatg  tattgcgaga      540
gaaagccaag  gccttctggg  ccctgaggcg  cacctatgag  gccattgcca  agcacaatga      600
ggtgcaaacg  acttggctgg  aaggccgcat  ccgggatgag  tttgacaagc  tccgtgattt      660
cctgagggtg  gaggaacagg  ccaccttgga  tgccatgaag  gaagagagca  gaaagaagca      720
cctgcaggct  gaggagaaga  tgaagcagct  agcagaacag  accgaggcgc  tggctcggga      780
gattgagcgt  ctgcagatgg  agatgaagga  agatgacatg  accttcctca  tgaaacacaa      840
gagccgaaaa  cgccggctct  tctgcaccgt  ggagccagct  cctctccagc  ctggcttgct      900
aatggatgca  tgcaagtatc  tggagtccct  gcagtaccga  gtctggaaga  agatgcttgg      960
atccgttgag  tctgtgccct  tcagcttgga  tcccaacaca  gctgctggct  ggctcaaagt     1020
ggctgatgac  ctcacgagtg  tcatcaacca  tggctaccgc  gtgcaagtgg  agaatccaga     1080
gcgcttctcc  tcggcaccct  gcctgctagg  ctctcaagtt  ttctccaagg  ctcccactc      1140
ttgggaggtg  gatgtgggtg  gcctgccaac  ctggcgagtg  gtgtgtggttc  gggtgcaggc     1200
acatgcacag  gcgcaggctc  aggctgacgt  aggtggtgaa  ggccactcac  acagctgcta     1260
ccatgataca  cgctcaggct  ctggtacctt  gtgccgcacg  cagggtgtgg  atggagacca     1320
ctgcatgact  tccgacactg  ccacagcccc  tctggtccag  gccatgccgc  gccgtctgcg     1380
tgtggagctg  gagtgtgagg  agggtgagct  atccttctat  gactctgagc  gccactgcca     1440
tctgtatacc  ttccatgccc  actttgggga  ggtgaggccc  tacttctacc  tgggagcctc     1500
tcgaggtgac  ggtccccgg   aacctctgcg  tatctgccac  ctgcgtgtct  ccatcaaaga     1560
agagctggac  atctgagctg  cccacccctg  acacatgcag  catactatat  cctgtcttag     1620
cttttctgta  gctccaaagt  taggagccac  ccaggaggtg  cttggctgag  cctaggctct     1680
gtctacagtc  atgctacctt  caggatgtgg  gttttctgtt  cttggattgc  tggtatactg     1740
ttttctttgt  aggatggcat  tataatgtag  gtgtagacta  ttttagaga   tgatgaagcc     1800
agcctatcag  gagatgcctc  ttattgagtc  tatttgtcat  ttatgtttcc  caggaagagg     1860
tccttgtcag  gccacacagg  gaagccccag  gatggtttga  gacaagagtg  ggcaaagcct     1920
tcacctaggc  tctcccaccc  cagtaggaca  agttaggtat  tggccagcct  cactgagcta     1980
tgcatggctt  tagcatctgg  tctgaaccag  gagtccccgt  gttggttcct  aggacaggat     2040
```

-continued

```
tgtccttgac tctctctgtg ggaacactgt agggtgtgag gtactctgga atacagctca    2100
gagttgtggg tgtctcagga aaggcagctc cagggccttt ggcagtggtt aaggactgac    2160
cagcctcaag ttagtgccat agaggccaaa gcaccagaat gcagtgagtg agaagacagc    2220
tagtgctggg ttgaacatg agccccactc tgttactcag tctttcggca cggaatcgac     2280
actggttggt cacctcatgc tttgaacgtt tcctctggaa ttgtccagtt ttctagaaca    2340 cttttaaac ctgtgtttcc acatctgtga tttgacacta gtccttggaa atcactggag     2400
gaaggtatga gaaggagcct cagagaatgc tgcttcagtc agtgactgtt gtcttcattg    2460
gcttccacct gcctgtcctt gctctgctct ctgcagattc cacccctttc ctttatgtgt    2520
ccctctgcct tttctttctc agtcatgcct gtagatggag tctaattgcc aactaaccaa    2580
atcccaagag atgttgtaag gaaaaaatac catctcaggg gtgccctgtc atcgtcaaga    2640
cctaggacct agcatcccaa tttcagcctg caccctcat tacataagac ttgttttaaa    2700
ccacgccgat tacccactaa ttggctctaa atgggtcatg tgcacttgtg gattatctaa    2760
caagtggaga cacagaagaa accctggtgc aggccaggcc gggagcaggg acagtgttgg   2820
caagccagct tgtgagtgtc agatgcttgg gcaccacgga tgtgaaaggt gcgcctggtg    2880
caatgtatgt gtttggttaa agaaactctc tgaaattact gttataataa gttttaaaa    2940 gtttttctt tctttttaat tttcaccta actcttaaat agggtaattt caatgaccta      3000
gactcttaga aaaatttga cttaccccac aactgacatg tttctttcag gcttttgta     3060 aacacaaatt cctagtgtaa cttgtacctg atctgtcctt cccattgtaa gattccatcg    3120
tgtgcagtga atgtgctgtg caacttgtta gttgatggac atttggcttg ttgcagtgtg    3180
tttagctgtt atgagttctg ctgctatgaa atttgtgtgc aagttttgtg tggctgtgtc    3240
tcttgatttt ctgtcatata ccttggagtc tgttttccag gtcatatgat aattattta    3300 agcccttgg ggacttgcca agctgttct aagagagccg tcccattttc tactcccacc      3360
ggcagcaggt gagggctggt ttgtaacgaa ttctctctgc cctcttaagc tgaggaagct    3420
ggagtaggtc tcatttgccc tgtagttgcg atctctgatg gctggggagc atctttcctc    3480
atgtttgctg tgtatctgct tcagagactt cagggtgttt gcccattggg ttgtctgacc    3540
ttttattatg aaggtttaca agtttgttat gcattctaga taaagttcc tttgtgtcag     3600 atgaatcaca taaaaatttt cctcctaatt caaaaaaaaa aaaaaaa                  3648
```

<210> SEQ ID NO 2
<211> LENGTH: 516
<212> TYPE: PRT
<213> ORGANISM: Mus musculus

<400> SEQUENCE: 2

```
Met Lys Ala Ala Thr Pro Val Val Thr Ala Ala Ala Pro Ala Met
1               5                   10                  15

Glu Pro Gly Pro Ser Val Ser Pro Gly Pro Ser Arg Ser Phe Lys Glu
            20                  25                  30

Glu Leu Leu Cys Ala Val Cys Tyr Asp Pro Phe Arg Asp Ala Val Thr
        35                  40                  45

Leu Arg Cys Gly His Asn Phe Cys Arg Cys Val Ser Gly Cys Trp
    50                  55                  60

Glu Val Gln Thr Thr Pro Ser Cys Pro Val Cys Lys Glu Arg Ala Val
65                  70                  75                  80

Pro Gly Glu Leu Arg Thr Asn His Thr Leu Asn Asn Leu Val Glu Thr
                85                  90                  95
```

-continued

```
Leu Leu Arg Glu Glu Ala Gly Ala Arg Trp Thr Gly Arg Arg Ser
            100                 105                 110

Pro Arg Pro Cys Arg Ala His Arg Ala Pro Leu Thr Leu Phe Cys Leu
        115                 120                 125

Glu Asp Lys Glu Leu Leu Cys Cys Ala Cys Gln Ala Asp Ala Arg His
130                 135                 140

Gln Glu His Arg Val Gln Pro Ile Lys Asp Thr Ala Gln Asp Phe Arg
145                 150                 155                 160

Ala Lys Cys Lys Asn Met Glu His Val Leu Arg Glu Lys Ala Lys Ala
                165                 170                 175

Phe Trp Ala Leu Arg Arg Thr Tyr Glu Ala Ile Ala Lys His Asn Glu
            180                 185                 190

Val Gln Thr Thr Trp Leu Glu Gly Arg Ile Arg Asp Glu Phe Asp Lys
        195                 200                 205

Leu Arg Asp Phe Leu Arg Val Glu Glu Gln Ala Thr Leu Asp Ala Met
        210                 215                 220

Lys Glu Glu Ser Arg Lys Lys His Leu Gln Ala Glu Lys Met Lys
225                 230                 235                 240

Gln Leu Ala Glu Gln Thr Glu Ala Leu Ala Arg Glu Ile Glu Arg Leu
                245                 250                 255

Gln Met Glu Met Lys Glu Asp Asp Met Thr Phe Leu Met Lys His Lys
            260                 265                 270

Ser Arg Lys Arg Arg Leu Phe Cys Thr Val Glu Pro Ala Pro Leu Gln
        275                 280                 285

Pro Gly Leu Leu Met Asp Ala Cys Lys Tyr Leu Glu Ser Leu Gln Tyr
    290                 295                 300

Arg Val Trp Lys Lys Met Leu Gly Ser Val Glu Ser Val Pro Phe Ser
305                 310                 315                 320

Leu Asp Pro Asn Thr Ala Ala Gly Trp Leu Lys Val Ala Asp Asp Leu
                325                 330                 335

Thr Ser Val Ile Asn His Gly Tyr Arg Val Gln Val Glu Asn Pro Glu
            340                 345                 350

Arg Phe Ser Ser Ala Pro Cys Leu Leu Gly Ser Gln Val Phe Ser Lys
        355                 360                 365

Gly Ser His Ser Trp Glu Val Asp Val Gly Gly Leu Pro Thr Trp Arg
    370                 375                 380

Val Gly Val Val Arg Val Gln Ala His Ala Gln Ala Gln Ala
385                 390                 395                 400

Asp Val Gly Gly Glu Gly His Ser His Ser Cys Tyr His Asp Thr Arg
                405                 410                 415

Ser Gly Phe Trp Tyr Leu Cys Arg Thr Gln Gly Val Asp Gly Asp His
            420                 425                 430

Cys Met Thr Ser Asp Thr Ala Thr Ala Pro Leu Val Gln Ala Met Pro
        435                 440                 445

Arg Arg Leu Arg Val Glu Leu Glu Cys Glu Glu Gly Glu Leu Ser Phe
    450                 455                 460

Tyr Asp Ser Glu Arg His Cys His Leu Tyr Thr Phe His Ala His Phe
465                 470                 475                 480

Gly Glu Val Arg Pro Tyr Phe Tyr Leu Gly Ala Ser Arg Gly Asp Gly
                485                 490                 495

Pro Pro Glu Pro Leu Arg Ile Cys His Leu Arg Val Ser Ile Lys Glu
        500                 505                 510

Glu Leu Asp Ile
        515
```

<210> SEQ ID NO 3
<211> LENGTH: 4181
<212> TYPE: DNA
<213> ORGANISM: Homo sapiens

<400> SEQUENCE: 3

```
aaagttccgg gcgcccgagc cggctgctcg tgccatggag cggagtcccg acgtgtcccc      60
cgggccttcc cgctccttca aggaggagtt gctctgcgcc gtctgctacg accccttccg     120
cgacgcagtc actctgcgct gcggccacaa cttctgccgc gggtgcgtga ccgctgctg     180
ggaggtgcag gtgtcgccca cctgcccagt gtgcaaagac cgcgcgtcac ccgccgacct     240
gcgcaccaac cacaccctca caacctggt ggagaagctg ctgcgcgagg aggccgaggg     300
cgcgcgctgg accagctacc gcttctcgcg tgtctgccgc ctgcaccgcg acagctcag     360
cctcttctgc ctcgaggaca aggagctgct gtgctgctcc tgccaggccg accccgaca    420
ccaggggcac cgcgtgcagc cggtgaagga cactgcccac gactttcggg ccaagtgcag     480
gaacatggag catgcactgc gggagaaggc caaggccttc tgggccatgc ggcgctccta     540
tgaggccatc gccaagcaca atcaggtgga ggctgcatgg ctggaaggcc ggatccggca     600
ggagtttgat aagcttcgcg agttcttgag agtggaggag caggccattc tggatgccat     660
ggccgaggag acaaggcaga agcaacttct ggccgacgag aagatgaagc agctcacaga     720
ggagacggag gtgctggcac atgagatcga gcggctgcag atggagatga aggaggacga     780
cgtttctttt ctcatgaaac acaagagccg aaaacgccga ctcttctgca ccatggagcc     840
agagccagtc cagcccggca tgcttatcga tgtctgcaag tacctgggct ccctgcagta     900
ccgcgtctgg aagaagatgc ttgcatctgt ggaatctgta cccttcagct ttgaccccaa     960
caccgcagct ggctggctct ccgtgtctga cgacctcacc agcgtcacca accatggcta    1020
ccgcgtgcag gtggagaacc cggaacgctt ctcctcggcg ccctgcctgc tgggctcccg    1080
tgtcttctca cagggctcgc acgcctggga ggtggccctt gggggggctgc agagctggag    1140
ggtgggcgtg gtacgtgtgc gccaggactc gggcgctgag ggccactcac acagctgcta    1200
ccacgacaca cgctcgggct tctggtatgt ctgccgcacg cagggcgtgg aggggggacca    1260
ctgcgtgacc tcggacccag ccacgtcgcc cctggtcctg gccatcccac gccgcctgcg    1320
tgtggagctg gagtgtgagg agggcgagct gtctttctat gacgcggagc gccactgcca    1380
cctgtacacc ttccacgccc gctttgggga ggttcgcccc tacttctacc tgggggggtgc    1440
acggggcgcc gggcctccag agcctttgcg catctgcccc ttgcacatca gtgtcaagga    1500
agaactggat ggctgagctg gcccggggct gccccggtct tgtgccacag cactgttttc    1560
tttctgccct cttcctaatg cccacactgc ttgggcacta ttgcgcccct gcctccttgc    1620
caggctcttc ctcctgtcct gcctggtcct tttccatgac tccaggctgt gcctctctcc    1680
atgtttggtc ccttctgtgc ccatggtcag gagctattcg ggtggcacct cgctggccag    1740
gctctcccga gtcgtggcac ctccacaatg tgaattttct gaatccctat tccaggattt    1800
ctgggaataa tgtttacttc tagaatgggc tgttgtaaa ccatctcatc gaggtgtggt    1860
aaagccattg gatgaggagg ggactgccat ggaaaggaga gtttgttact acggttctg    1920
agaggagggg ccacatagga aagccccacg gtgggtcaga aggcggaagg agggagggga    1980
acgtgtgggc aagagacttc ctctggtttc ctcaggagga aatgggcaag gcagagtaag    2040
caggggagac aggtttaagg gtagctggct tgagtaattt cagtggctct caggataggg    2100
gctgcccttt ttgtctgata cctggccccg ggatagtcag gacaggtgaa tgttggcctg    2160
```

-continued

```
gggtgtgaca gccctgggag agccatgtga aggaggcagc tggcgccatc gctccggatt      2220
agttggtttc cataggaaag gcatgctttc agccagatgc ttgccatctc tagggattgg      2280
gggattggct agcctgggag gatcagtctg tccaggtcag cgaggcccca gataccagag      2340
catcaagagt acaggaaata cagttaatgc agggcctctg tgtggctgga tcctccgtct      2400
ccatcagatc agctctgatt gatctattct tgcacgattt cctctgaaca cagggttcca      2460
gagtacttaa acacaacatt ttttaaatcg tgatttcggc ctatttcctt gccaggcctg      2520
tttccccacc aggaaatgag ataggaggac tggatgagga tgtcctgtta tagttgctgt      2580
ggaggaagtt cctctggtta attctcatca gcgtctgcag aaaagaagga aagagggcac      2640
ccttttcagt tgggaagaaa ggagaggggt ggcgccatgg acgtggccct aaacgctgtg      2700
ggagagggaa gaggaggctg ggcctcgctg ccctcttgtc tctgctgact tcagcctggt      2760
catgcttgct ctgccacttg cgatttcatc cctaatttct tcctccacca tgcctgcaga      2820
cttttccctg ggcttgtttt ttctcgcaca tctctgaaga gttttaatc ttcagctcat       2880 catgtcccag gaagtggcat cataaaagga aatatttttt tttcctagga gcagtgttaa      2940
aatctgggtc acattcctga ccaaggacag catcctgcct tctgcccatc ccttcagtt       3000 cacaaaagct gacattttaa acaaatcatg actcacacgt attaattggt tataaatatg      3060
ttgtgtacac tggttagata aacttaagg ccacaaggag ggcccaggta ggcgatgtca       3120
gtgtgtgaag gggctggatt gggcgtggtg aggatgttgg caaaccagtg catgcacctg      3180
gttggaagat gctcagcctc acaaaagctc caagcccttt gggagccaaa gtgtctgaga      3240
gtgtgaccct ctcctgtaaa gtatttatcc cacccattaa tataatttct gtataataaa      3300
cttgacctga aattatttca ttctttatat taaacttttta aaaatgtttt ttattttcac     3360
cttagatatg ggaagagttt ttttttttt tttttttttt taacaggata acttgagcag      3420
gctaggcctc ttaaaaaaaa atttgagcta aaactcattt ttcttttggc attttctttt      3480
caatgttctt ataagcaaag ttcatccatg ttgtagcatg tgttcaactt tattttttca     3540
tcgggtaata ttccattgta tggaatggta gtactacatt ttatttatca tgcatcgatt      3600
ggtggacatt tggatcgttt ctacttcttg actattatac ataatgctgc taggaacttt     3660
tgtgtatgag ttttgtgtg gacatatgtt ttcattctc tttggtatat gcctgggagc       3720
agatttgctg gatcatatga aactctattt aacccttgag ggactcccaa actgttttcc     3780
aatgtggtga cacaatttta tatcccatca acagggcatg agggttctga tgactccaca     3840
tccctcagtg cttttatta tctatctttt aacttagcca tcctagtagg ggtaatgtgg      3900
catctcattg tgattttggt ttgcattcc ctgatggcga atgatattga gcatcttttc     3960
atgagcttat tggccatttg catatcttct taggacagct atctttagat cacttgctca     4020
ttttttaatt gggttatttg tctttttatt attgagttgt aagagtcctt ttatagcctg     4080
gcacaagtcc ctttaactgg tatatgatta taaaattttt ctccgtgagc tgtttcattt     4140
ccttgatgat gtcctttgaa atactaaagc ttttaatttt g                          4181
```

<210> SEQ ID NO 4
<211> LENGTH: 504
<212> TYPE: PRT
<213> ORGANISM: Homo sapiens

<400> SEQUENCE: 4

Lys Phe Arg Ala Pro Glu Pro Ala Ala Arg Ala Met Glu Arg Ser Pro
1               5                   10                  15

```
Asp Val Ser Pro Gly Pro Ser Arg Ser Phe Lys Glu Glu Leu Leu Cys
         20                  25                  30
Ala Val Cys Tyr Asp Pro Phe Arg Asp Ala Val Thr Leu Arg Cys Gly
             35                  40                  45
His Asn Phe Cys Arg Gly Cys Val Ser Arg Cys Trp Glu Val Gln Val
 50                  55                  60
Ser Pro Thr Cys Pro Val Cys Lys Asp Arg Ala Ser Pro Ala Asp Leu
 65                  70                  75                  80
Arg Thr Asn His Thr Leu Asn Asn Leu Val Glu Lys Leu Leu Arg Glu
                 85                  90                  95
Glu Ala Glu Gly Ala Arg Trp Thr Ser Tyr Arg Phe Ser Arg Val Cys
            100                 105                 110
Arg Leu His Arg Gly Gln Leu Ser Leu Phe Cys Leu Glu Asp Lys Glu
            115                 120                 125
Leu Leu Cys Cys Ser Cys Gln Ala Asp Pro Arg His Gln Gly His Arg
        130                 135                 140
Val Gln Pro Val Lys Asp Thr Ala His Asp Phe Arg Ala Lys Cys Arg
145                 150                 155                 160
Asn Met Glu His Ala Leu Arg Glu Lys Ala Lys Ala Phe Trp Ala Met
                165                 170                 175
Arg Arg Ser Tyr Glu Ala Ile Ala Lys His Asn Gln Val Glu Ala Ala
            180                 185                 190
Trp Leu Glu Gly Arg Ile Arg Gln Glu Phe Asp Lys Leu Arg Glu Phe
        195                 200                 205
Leu Arg Val Glu Glu Gln Ala Ile Leu Asp Ala Met Ala Glu Glu Thr
        210                 215                 220
Arg Gln Lys Gln Leu Leu Ala Asp Glu Lys Met Lys Gln Leu Thr Glu
225                 230                 235                 240
Glu Thr Glu Val Leu Ala His Glu Ile Glu Arg Leu Gln Met Glu Met
                245                 250                 255
Lys Glu Asp Asp Val Ser Phe Leu Met Lys His Lys Ser Arg Lys Arg
            260                 265                 270
Arg Leu Phe Cys Thr Met Glu Pro Glu Pro Val Gln Pro Gly Met Leu
        275                 280                 285
Ile Asp Val Cys Lys Tyr Leu Gly Ser Leu Gln Tyr Arg Val Trp Lys
290                 295                 300
Lys Met Leu Ala Ser Val Glu Ser Val Pro Phe Ser Phe Asp Pro Asn
305                 310                 315                 320
Thr Ala Ala Gly Trp Leu Ser Val Ser Asp Asp Leu Thr Ser Val Thr
                325                 330                 335
Asn His Gly Tyr Arg Val Gln Val Glu Asn Pro Glu Arg Phe Ser Ser
            340                 345                 350
Ala Pro Cys Leu Leu Gly Ser Arg Val Phe Ser Gln Gly Ser His Ala
        355                 360                 365
Trp Glu Val Ala Leu Gly Gly Leu Gln Ser Trp Arg Val Gly Val Val
        370                 375                 380
Arg Val Arg Gln Asp Ser Gly Ala Glu Gly His Ser His Ser Cys Tyr
385                 390                 395                 400
His Asp Thr Arg Ser Gly Phe Trp Tyr Val Cys Arg Thr Gln Gly Val
            405                 410                 415
Glu Gly Asp His Cys Val Thr Ser Asp Pro Ala Thr Ser Pro Leu Val
            420                 425                 430
Leu Ala Ile Pro Arg Arg Leu Arg Val Glu Leu Glu Cys Glu Glu Gly
        435                 440                 445
```

Glu Leu Ser Phe Tyr Asp Ala Glu Arg His Cys His Leu Tyr Thr Phe
    450                 455                 460

His Ala Arg Phe Gly Glu Val Arg Pro Tyr Phe Tyr Leu Gly Gly Ala
465                 470                 475                 480

Arg Gly Ala Gly Pro Pro Glu Pro Leu Arg Ile Cys Pro Leu His Ile
            485                 490                 495

Ser Val Lys Glu Glu Leu Asp Gly
        500

<210> SEQ ID NO 5
<211> LENGTH: 361
<212> TYPE: DNA
<213> ORGANISM: Mus musculus

<400> SEQUENCE: 5
gatcgcaact acagggcaga tgagacctac tccagcttcc tcagcttaag aggcagagag      60
aattcgttac gaaccagccc tcacctgctg ccggtgggag tagaaaatgg gacggctctc     120
ttagaaacag cttggcaggt ccccaaatgg cttaaaataa ttatcatatg acctggaaaa     180
cagactccaa ggtatatgac agaaaatcaa gagacacagc cacacaaaac ttgcttacaa     240
acttcatagc agcagaactc ataacagcta acacactgc aacaagccaa atgtccatca      300
actacaagtt gcacaacaca ttcactgcac acgatggaat tttacaatgg aaggacaga     360 t                                                                    361

<210> SEQ ID NO 6
<211> LENGTH: 2358
<212> TYPE: DNA
<213> ORGANISM: Homo sapiens

<400> SEQUENCE: 6
gagatcgagc ggctgcagat ggagatgaag gaggacgacg tttcttttct catgaaacac      60
aagagccgaa acgccggta agttgccaaa gctggtggag gggaggggaa gagtgggcag     120
aaataccagg ggtgcaaact ccagtggccc cggggcaagc aggtaacaac cagctgggtg     180
caccagcaca catgagctac tggccctggt tttagaggga gaggtggaca atggccaggt     240
ggagagagcc ctctcacagc atccagttca agttggctct ggggcagcgt tgttctcctg     300
agtgtggagg gtccccacct gccgtgcagg gaaggagaac actatcctgc atgtggcttg     360
catttctcgg ggccagtcaa tgtcaggctt gtttcttgat cagccccctc cctctgagag     420
ccttaggcca tggtggtttg tgctgatggt tgttgggttc acagggatga atgaggaaga     480
gctgtgtccc agtcagagct gtgcaaagat ggaatagagt gcttttggag ggagtgagtt     540
ccctgtgctc acttcccact ggcagtgtgc aagcaaaggc tggaggacac cttgggattg     600
ttggactaga gcatccttag ggtcccttcc aactcagaca tcccatgagc cggatgtgta     660
agtgtgattt ctgcctgcaa ggatggcagc catgttggag aacctcctgt ttgtatttct     720
cctagttggg gcagggtgag ccctcggatt gaatgctgaa gggagatggc agccctgttg     780
gccttggccc atctcccatc gtagcccagt ccagtcttgt cttggagaag gtggccagga     840
aacttgggcc tgagggaagg gaacaagtcc tgttgctggt ttccagttgg cccagttcgg     900
cccaggttgc atggctctgg ccctgcccac ataccccatt gtacttttcc agactctttct     960 gcaccatgga gccagagcca gtccagcccg gcatgcttat cgatgtctgc aagtacctgg    1020
gctccctgca gtatcgcgtc tggaagaagg tgcttgcatc tgtggaatct ggtgagcggg    1080
ggtgccggca ggtgtcccaa gcatgggtgg aagcccttca tgttagcaaa gaggcaccag    1140

```
ggctggtctc tgccgggccc acctcccacc tcctcagagc tccctcctc tctcagctga    1200 tccctctgcc agtccctcgc aggcaggttc ctgtaccctg gtcttttcca ctctgcccaa    1260
cacctccaac cctcctggta gaatgccttc tctcagggtc ctgacacttg gtcccttctt    1320
cagagaggga aactggcttt cttgcctatt cagaactgtg ttttgtatga taaaagacct    1380
cctgcatctg ggcctgcctc tcccaaggcg actgcagccc acatgagcca cagtgtcctg    1440
gttttacggg gaggaatatc actgactcag gaatgggccg tgctgtccta acatcccctt    1500
ggtcgtgtga gtgttaagag tctctgcctg tatgagttcc tgtggctgcc ataacgaagg    1560
accacaaact agaaaatgac agaagttgac tctctcacag ttctggaggg tagaaatcca    1620
aaatccagat gttggaagga ccaggccccc tctgaaacct gtagaggaga gtcttcattt    1680
cctcttccgt ctcctggtgt ctcctggcca ttcttggcct tattggctcc ccctcagcac    1740
tttgatcctc acctccgcca tcacacagca ttctcccctg tgtatctgtg tctgtctcct    1800
ctttatttta aggacacagg tcatattgga ttggggaccc tcctccagtc ttcatcttaa    1860
ctaatatgtg tacaaccacc ccattcccaa ataaggtcac actcggaggt accaggggtt    1920
gggactgccg catatcttct gggggataca gcccaacccc tgccaccact ccagcctggg    1980
ccactccttg catggacttg gggccaggtg tgacacagtg gttggtttgt ggggctggag    2040
atatccacgt gtggctaagg gacctcaggg ttgctgattc cccatttccg cctctgcttg    2100 cagtacccctt cagctttgac cccaacaccg cagctggctg ctctccgtg tctgacgacc    2160 tcaccagcgt caccaaccat ggctaccgcg tgcaggtgga gaacccggaa cgcttctcct    2220
cggcgccctg cctgctgggc tcccgtgtct tctcacaggg ctcgcacgcc tgggaggtgg    2280
cccttggggg gctgcagagc tggagggtgg gcgtggtacg tgtgcgccag gactcgggcg    2340
ctgagggcca ctcacaca                                                 2358
```

<210> SEQ ID NO 7
<211> LENGTH: 4801
<212> TYPE: DNA
<213> ORGANISM: Homo sapiens
<220> FEATURE:
<221> NAME/KEY: CDS
<222> LOCATION: (655)..(2133)

<400> SEQUENCE: 7

```
cttttttcaac cacaggacaa gaatcaggtt ttctcggagc tcttctgccg ccacccctct     60
cttgtttctc cttaccgcgg cgggccagaa gaagactggc caaaataagt aaacgactaa    120
tgcaagagtg gcataggtcc tcaaaaaggc gctgcaaact taagtggtga ttgcactcac    180
ggtgctttaa gacccagcca ctacttcgga agcaggaagt tggcatctct ggtttctccc    240
atccgcgggc ctgaggttcc cggggattgg ttaaggtaga ggctcctttt cccatttgca    300 gccgaagta ggtttccagt aacacggaag ccctactacg ccgcctggga gacccttccg     360
tgctaccccg gccagggacc cgcccggacc tgaggaggcg ggaactgcgg gcagaaggcc    420
caccccgctc tccaagagat tccgcgcac accggaagtg ggtggggctc ctccgagcgc    480 ccccctcccctc cccctcgcca tcccccccgc acgattggcc agcgccgctg tctctcagcg    540
ttccagggga agggactggg cgattcccag cactcgggtc gcgggcgttg gcagccgggc    600
gggtgggagg ggccggagca aaagttccgg gcgcccgagc cggctgctcg tgcc atg      657
                                                                    Met
                                                                     1 gag cgg agt ccc gac gtg tcc ccc ggg cct tcc cgc tcc ttc aag gag    705
Glu Arg Ser Pro Asp Val Ser Pro Gly Pro Ser Arg Ser Phe Lys Glu
```

```
                5                    10                   15
gag ttg ctc tgc gcc gtc tgc tac gac ccc ttc cgc gac gca gtc act    753
Glu Leu Leu Cys Ala Val Cys Tyr Asp Pro Phe Arg Asp Ala Val Thr
         20                  25                  30 ctg cgc tgc ggc cac aac ttc tgc cgc ggg tgc gtg agc cgc tgc tgg    801
Leu Arg Cys Gly His Asn Phe Cys Arg Gly Cys Val Ser Arg Cys Trp
 35                  40                  45 gag gtg cag gtg tcg ccc acc tgc cca gtg tgc aaa gac cgc gcg tca    849
Glu Val Gln Val Ser Pro Thr Cys Pro Val Cys Lys Asp Arg Ala Ser
50                   55                  60                  65 ccc gcc gac ctg cgc acc aac cac acc ctc aac aac ctg gtg gag aag    897
Pro Ala Asp Leu Arg Thr Asn His Thr Leu Asn Asn Leu Val Glu Lys
         70                  75                  80 ctg ctg cgc gag gag gcc gag ggc gcg cgc tgg acc agc tac cgc ttc    945
Leu Leu Arg Glu Glu Ala Glu Gly Ala Arg Trp Thr Ser Tyr Arg Phe
 85                  90                  95 tcg cgt gtc tgc cgc ctg cac cgc gga cag ctc agc ctc ttc tgc ctc    993
Ser Arg Val Cys Arg Leu His Arg Gly Gln Leu Ser Leu Phe Cys Leu
         100                 105                 110 gag gac aag gag ctg ctg tgc tgc tcc tgc cag gcc gac ccc cga cac   1041
Glu Asp Lys Glu Leu Leu Cys Cys Ser Cys Gln Ala Asp Pro Arg His
115                  120                 125 cag ggg cac cgc gtg cag ccg gtg aag gac act gcc cac gac ttt cgg   1089
Gln Gly His Arg Val Gln Pro Val Lys Asp Thr Ala His Asp Phe Arg
130                  135                 140                 145 gcc aag tgc agg aac atg gag cat gca ctg cgg gag aag gcc aag gcc   1137
Ala Lys Cys Arg Asn Met Glu His Ala Leu Arg Glu Lys Ala Lys Ala
         150                 155                 160 ttc tgg gcc atg cgg cgc tcc tat gag gcc atc gcc aag cac aat cag   1185
Phe Trp Ala Met Arg Arg Ser Tyr Glu Ala Ile Ala Lys His Asn Gln
 165                 170                 175 gtg gag gct gca tgg ctg gaa ggc cgg atc cgg cag gag ttt gat aag   1233
Val Glu Ala Ala Trp Leu Glu Gly Arg Ile Arg Gln Glu Phe Asp Lys
         180                 185                 190 ctt cgc gag ttc ttg aga gtg gag gag cag gcc att ctg gat gcc atg   1281
Leu Arg Glu Phe Leu Arg Val Glu Glu Gln Ala Ile Leu Asp Ala Met
195                  200                 205 gcc gag gag aca agg cag aag caa ctt ctg gcc gac gag aag atg aag   1329
Ala Glu Glu Thr Arg Gln Lys Gln Leu Leu Ala Asp Glu Lys Met Lys
210                  215                 220                 225 cag ctc aca gag gag acg gag gtg ctg gca cat gag atc gag cgg ctg   1377
Gln Leu Thr Glu Glu Thr Glu Val Leu Ala His Glu Ile Glu Arg Leu
         230                 235                 240 cag atg gag atg aag gag gac gac gtt tct ttt ctc atg aaa cac aag   1425
Gln Met Glu Met Lys Glu Asp Asp Val Ser Phe Leu Met Lys His Lys
 245                 250                 255 agc cga aaa cgc cga ctc ttc tgc acc atg gag cca gag cca gtc cag   1473
Ser Arg Lys Arg Arg Leu Phe Cys Thr Met Glu Pro Glu Pro Val Gln
         260                 265                 270 ccc ggc atg ctt atc gat gtc tgc aag tac ctg ggc tcc ctg cag tac   1521
Pro Gly Met Leu Ile Asp Val Cys Lys Tyr Leu Gly Ser Leu Gln Tyr
275                  280                 285 cgc gtc tgg aag aag atg ctt gca tct gtg gaa tct gta ccc ttc agc   1569
Arg Val Trp Lys Lys Met Leu Ala Ser Val Glu Ser Val Pro Phe Ser
290                  295                 300                 305 ttt gac ccc aac acc gca gct ggc tgg ctc tcc gtg tct gac gac ctc   1617
Phe Asp Pro Asn Thr Ala Ala Gly Trp Leu Ser Val Ser Asp Asp Leu
         310                 315                 320 acc agc gtc acc aac cat ggc tac cgc gtg cag gtg gag aac ccg gaa   1665
Thr Ser Val Thr Asn His Gly Tyr Arg Val Gln Val Glu Asn Pro Glu
```

```
                      325                 330                 335
cgc ttc tcc tcg gcg ccc tgc ctg ctg ggc tcc cgt gtc ttc tca cag   1713
Arg Phe Ser Ser Ala Pro Cys Leu Leu Gly Ser Arg Val Phe Ser Gln
            340                 345                 350 ggc tcg cac gcc tgg gag gtg gcc ctt ggg ggg ctg cag agc tgg agg   1761
Gly Ser His Ala Trp Glu Val Ala Leu Gly Gly Leu Gln Ser Trp Arg
        355                 360                 365 gtg ggc gtg gta cgt gtg cgc cag gac tcg ggc gct gag ggc cac tca   1809
Val Gly Val Val Arg Val Arg Gln Asp Ser Gly Ala Glu Gly His Ser
370                 375                 380                 385 cac agc tgc tac cac gac aca cgc tcg ggc ttc tgg tat gtc tgc cgc   1857
His Ser Cys Tyr His Asp Thr Arg Ser Gly Phe Trp Tyr Val Cys Arg
                390                 395                 400 acg cag ggc gtg gag ggg gac cac tgc gtg acc tcg gac cca gcc acg   1905
Thr Gln Gly Val Glu Gly Asp His Cys Val Thr Ser Asp Pro Ala Thr
            405                 410                 415 tcg ccc ctg gtc ctg gcc atc cca cgc cgc ctg cgt gtg gag ctg gag   1953
Ser Pro Leu Val Leu Ala Ile Pro Arg Arg Leu Arg Val Glu Leu Glu
        420                 425                 430 tgt gag gag ggc gag ctg tct ttc tat gac gcg gag cgc cac tgc cac   2001
Cys Glu Glu Gly Glu Leu Ser Phe Tyr Asp Ala Glu Arg His Cys His
435                 440                 445 ctg tac acc ttc cac gcc cgc ttt ggg gag gtt cgc ccc tac ttc tac   2049
Leu Tyr Thr Phe His Ala Arg Phe Gly Glu Val Arg Pro Tyr Phe Tyr
450                 455                 460                 465 ctg ggg ggt gca cgg ggc gcc ggg cct cca gag cct ttg cgc atc tgc   2097
Leu Gly Gly Ala Arg Gly Ala Gly Pro Pro Glu Pro Leu Arg Ile Cys
                470                 475                 480 ccc ttg cac atc agt gtc aag gaa gaa ctg gat ggc tgagctggcc        2143
Pro Leu His Ile Ser Val Lys Glu Glu Leu Asp Gly
            485                 490 cggggctgcc ccggtcttgt gccacagcac tgttttcttt ctgccctctt cctaatgccc   2203
acactgcttg ggcactattg cgcccctgcc tccttgccag gctcttcctc ctgtcctgcc   2263
tggtcctttt ccatgactcc aggctgtgcc tctctccatg tttggtccct tctgtgccca   2323
tggtcaggag ctattcgggt ggcacctcgc tggccaggct ctcccgagtc gtggcacctc   2383
cacaatgtga attttctgaa tccctattcc aggatttctg gaataatgt ttacttctag    2443
aatgggcctg ttgtaaacca tctcatcgag gtgtggtaaa gccattggat gaggagggga   2503
ctgccatgga aaggagagtt tgttacttac ggttctgaga ggaggggcca cataggaaag   2563
ccccacggtg ggtcagaagg cggaaggagg gaggggaacg tgtgggcaag agacttcctc   2623
tggtttcctc aggaggaaat gggcaaggca gagtaagcag gggagacagg tttaagggta   2683
gctggcttga gtaatttcag tggctctcag gatagggggct gcccttttttg tctgataacct   2743
ggccccggga tagtcaggac aggtgaatgt tggcctgggg tgtgacagcc ctgggagagc   2803
catgtgaagg aggcagctgg cgccatcgct ccgattagt tggtttccat aggaaaggca   2863
tgctttcagc cagatgcttg ccatctctag ggattggggg attggctagc ctgggaggat   2923
cagtctgtcc aggtcagcga ggccccagat accagagcat caagagtaca ggaaatacag   2983
ttaatgcagg gcctctgtgt ggctggatcc tccgtctcca tcagatcagc tctgattgat   3043
ctattcttgc acgatttcct ctgaacacag ggttccagag tacttaaaca caacattttt   3103
taaatcgtga tttcggccta tttccttgcc aggcctgttt ccccaccagg aaatgagata   3163
ggaggactgg atgaggatgt cctgttatag ttgctgtgga ggaagttcct ctggttaatt   3223
ctcatcagcg tctgcagaaa agaaggaaag agggcaccct tttcagttgg gaagaaagga   3283
```

```
gagggggtggc gccatggacg tggccctaaa cgctgtggga gagggaagag gaggctgggc    3343
ctcgctgccc tcttgtctct gctgacttca gcctggtcat gcttgctctg ccacttgcga    3403
tttcatccct aatttcttcc tccaccatgc ctgcagactt ttccctgggc ttgtttttc     3463 tcgcacatct ctgaagagtt tttaatcttc agctcatcat gtcccaggaa gtggcatcat    3523
aaaaggaaat atttttttt cctaggagca gtgttaaaat ctgggtcaca ttcctgacca     3583
aggacagcat cctgccttct gcccatcccc ttcagttcac aaaagctgac atttttaaaca   3643 aatcatgact cacacgtatt aattggttat aaatatgttg tgtacactgg ttagataaaa    3703
cttaaggcca caaggagggc ccaggtaggc gatgtcagtg tgtgaagggg ctggattggg    3763
cgtggtgagg atgttggcaa accagtgcat gcacctggtt ggaagatgct cagcctcaca    3823
aaagctccaa gcccttgggg agccaaagtg tctgagagtg tgaccctctc ctgtaaagta    3883
tttatcccac ccattaatat aatttctgta taataaactt gacctgaaat tatttcattc    3943
tttatattaa acttttaaaa atgttttta ttttcacctt agatatggga agagtttttt    4003 ttttttttt tttttttaa caggataact tgagcaggct aggcctctta aaaaaaaatt      4063
tgagctaaaa ctcattttt ttttggcatt ttctttcaa tgttcttata agcaaagttc     4123
atccatgttg tagcatgtgt tcaactttat ttttcatcg ggtaatattc cattgtatgg    4183
aatggtagta ctacatttta tttatcatgc atcgattggt ggacatttgg atcgtttcta    4243
cttcttgact attatacata atgctgctag gaactttgt gtatgagttt ttgtgtggac    4303
atatgttttc atttctcttt ggtatatgcc tgggagcaga tttgctggat catatgaaac   4363
tctatttaac ccttgaggga ctcccaaact gttttccaat gtggtgacac aattttatat    4423
cccatcaaca gggcatgagg gttctgatga ctccacatcc ctcagtgctt tttattatct    4483
atcttttaac ttagccatcc tagtagggt aatgtggcat ctcattgtga ttttggtttg   4543
catttccctg atggcgaatg atattgagca tcttttcatg agcttattgg ccatttgcat    4603
atcttcttag gacagctatc tttagatcac ttgctcattt tttaattggg ttatttgtct    4663
ttttattatt gagttgtaag agtccttttta tagcctggca caagtcccctt taactggtat  4723 atgattataa aattttctc cgtgagctgt ttcatttcct tgatgatgtc ctttgaaata    4783
ctaaagcttt taattttg                                                 4801
```

<210> SEQ ID NO 8
<211> LENGTH: 493
<212> TYPE: PRT
<213> ORGANISM: Homo sapiens

<400> SEQUENCE: 8

```
Met Glu Arg Ser Pro Asp Val Ser Pro Gly Pro Ser Arg Ser Phe Lys
1               5                   10                  15

Glu Glu Leu Leu Cys Ala Val Cys Tyr Asp Pro Phe Arg Asp Ala Val
            20                  25                  30

Thr Leu Arg Cys Gly His Asn Phe Cys Arg Gly Cys Val Ser Arg Cys
        35                  40                  45

Trp Glu Val Gln Val Ser Pro Thr Cys Pro Val Cys Lys Asp Arg Ala
    50                  55                  60

Ser Pro Ala Asp Leu Arg Thr Asn His Thr Leu Asn Asn Leu Val Glu
65                  70                  75                  80

Lys Leu Leu Arg Glu Glu Ala Glu Gly Ala Arg Trp Thr Ser Tyr Arg
                85                  90                  95

Phe Ser Arg Val Cys Arg Leu His Arg Gly Gln Leu Ser Leu Phe Cys
            100                 105                 110
```

```
Leu Glu Asp Lys Glu Leu Leu Cys Cys Ser Cys Gln Ala Asp Pro Arg
            115                 120                 125
His Gln Gly His Arg Val Gln Pro Val Lys Asp Thr Ala His Asp Phe
            130                 135                 140
Arg Ala Lys Cys Arg Asn Met Glu His Ala Leu Arg Glu Lys Ala Lys
145                 150                 155                 160
Ala Phe Trp Ala Met Arg Arg Ser Tyr Glu Ala Ile Ala Lys His Asn
                165                 170                 175
Gln Val Glu Ala Ala Trp Leu Glu Gly Arg Ile Arg Gln Glu Phe Asp
            180                 185                 190
Lys Leu Arg Glu Phe Leu Arg Val Glu Gln Ala Ile Leu Asp Ala
            195                 200                 205
Met Ala Glu Glu Thr Arg Gln Lys Gln Leu Leu Ala Asp Glu Lys Met
            210                 215                 220
Lys Gln Leu Thr Glu Glu Thr Glu Val Leu Ala His Glu Ile Glu Arg
225                 230                 235                 240
Leu Gln Met Glu Met Lys Glu Asp Asp Val Ser Phe Leu Met Lys His
                245                 250                 255
Lys Ser Arg Lys Arg Arg Leu Phe Cys Thr Met Glu Pro Glu Pro Val
                260                 265                 270
Gln Pro Gly Met Leu Ile Asp Val Cys Lys Tyr Leu Gly Ser Leu Gln
            275                 280                 285
Tyr Arg Val Trp Lys Lys Met Leu Ala Ser Val Glu Ser Val Pro Phe
            290                 295                 300
Ser Phe Asp Pro Asn Thr Ala Ala Gly Trp Leu Ser Val Ser Asp Asp
305                 310                 315                 320
Leu Thr Ser Val Thr Asn His Gly Tyr Arg Val Gln Val Glu Asn Pro
                325                 330                 335
Glu Arg Phe Ser Ser Ala Pro Cys Leu Leu Gly Ser Arg Val Phe Ser
                340                 345                 350
Gln Gly Ser His Ala Trp Glu Val Ala Leu Gly Gly Leu Gln Ser Trp
            355                 360                 365
Arg Val Gly Val Val Arg Val Arg Gln Asp Ser Gly Ala Glu Gly His
            370                 375                 380
Ser His Ser Cys Tyr His Asp Thr Arg Ser Gly Phe Trp Tyr Val Cys
385                 390                 395                 400
Arg Thr Gln Gly Val Glu Gly Asp His Cys Val Thr Ser Asp Pro Ala
                405                 410                 415
Thr Ser Pro Leu Val Leu Ala Ile Pro Arg Arg Leu Arg Val Glu Leu
                420                 425                 430
Glu Cys Glu Glu Gly Leu Ser Phe Tyr Asp Ala Glu Arg His Cys
            435                 440                 445
His Leu Tyr Thr Phe His Ala Arg Phe Gly Glu Val Arg Pro Tyr Phe
            450                 455                 460
Tyr Leu Gly Gly Ala Arg Gly Ala Gly Pro Pro Glu Pro Leu Arg Ile
465                 470                 475                 480
Cys Pro Leu His Ile Ser Val Lys Glu Glu Leu Asp Gly
                485                 490

<210> SEQ ID NO 9
<211> LENGTH: 12
<212> TYPE: DNA
<213> ORGANISM: Artificial sequence
<220> FEATURE:
<223> OTHER INFORMATION: synthetic oligonucleotide
```

```
<400> SEQUENCE: 9
gatctgcggt ga                                                          12

<210> SEQ ID NO 10
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 10
agcactctcc agcctctcac cgca                                             24

<210> SEQ ID NO 11
<211> LENGTH: 12
<212> TYPE: DNA
<213> ORGANISM: Artificial sequence
<220> FEATURE:
<223> OTHER INFORMATION: synthetic oligonucleotide

<400> SEQUENCE: 11
gatctgttca tg                                                          12

<210> SEQ ID NO 12
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 12
accgacgtcg actatccatg aaca                                             24

<210> SEQ ID NO 13
<211> LENGTH: 12
<212> TYPE: DNA
<213> ORGANISM: Artificial sequence
<220> FEATURE:
<223> OTHER INFORMATION: synthetic oligonucleotide

<400> SEQUENCE: 13
gatcttccct cg                                                          12

<210> SEQ ID NO 14
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 14
aggcaactgt gctatccgag ggaa                                             24

<210> SEQ ID NO 15
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 15
gaaacacaag agccgaaaac gc                                               22

<210> SEQ ID NO 16
<211> LENGTH: 28
```

-continued

```
<212> TYPE: DNA
<213> ORGANISM: Artificial sequence
<220> FEATURE:
<223> OTHER INFORMATION: synthetic oligonucleotide

<400> SEQUENCE: 16
aagcctgagc gtgtatcatg gtagcagc                                        28
```

TUMOR SUPPRESSOR FACTOR

This application is a continuation of U.S. patent application Ser. No. 10/130,971, filed Sep. 26, 2002, now U.S. Pat. No. 7,560,253, issued Jul. 14, 2009, which is the U.S. National Phase of International Patent Application No. PCT/AU00/01439, filed Nov. 24, 2000, which claims priority to and the benefit of Australian Patent Application No. PQ 4216, filed Nov. 24, 1999, the contents of each of which are incorporated by reference herein.

FIELD OF THE INVENTION

The present invention relates generally to the field of tumour suppressor factors. Specifically, the present invention relates to a tumour suppressor gene and the amino acid sequence that it encodes. More specifically, the invention relates the use of the sequences, including mutations and alleles thereof, in the diagnosis of predisposition to tumour development where the identified suppressor factors are associated with tumour development. The invention also relates to the therapy of human cancers that have a mutation in the identified tumour suppressor gene, including gene therapy, protein replacement therapy and protein mimetics. The invention further relates to the screening of drugs for cancer therapy. Finally, the invention relates to the screening of the identified tumour suppressor gene for mutations, which are useful for diagnosing the predisposition to specific type of cancer.

BACKGROUND ART

Cancer is controlled by multiple dominant, positive regulators of the transformed state (oncogenes) as well as multiple recessive, negative regulators (tumour suppressor genes). In the oncogene family over one hundred different regulators have been characterised to date. In contrast, fewer than a dozen tumour suppressor genes have been characterised, however, this number is expected to increase beyond fifty.

The presence of so many genes involved in growth control mechanisms in cells underpins the complexity of the development of cancer and the complex processes that a cell has to maintain the integrity of normal tissue. This complexity is manifest in another way. So far, no single gene has been shown to participate in the development of all, or even the majority of human cancers. The most common oncogenic mutations are in the H-ras gene, found in 10-15% of all solid tumours. The most frequently mutated tumour suppressor genes are the p53 gene, homozygously deleted in roughly 50% of all tumors, and CDKN2, which was homozygously deleted in 46% of tumour cell lines examined.

The minor suppressor genes which have been cloned and characterized influence susceptibility to: 1) Retinoblastoma (RB1); 2) Wilms' tumour (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); 8) Multiple endocrine neoplasia type 2A (MEN2A); and 9) Melanoma (CDKN2).

Some of the tumour suppressor loci that have been mapped genetically but not yet isolated include genes for: Multiple endocrine neoplasia type 1 (MEN1); Lynch cancer family syndrome 2 (LCFS2); Neuroblastoma (NB); Beckwith-Wiedemann syndrome (BWS); Renal cell carcinoma (RCC); Tuberous sclerosis 1 (TSC1); and Tuberous sclerosis 2 (TSC2). The tumour suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), cell cycle regulators (CDKN2) and others with no obvious similarity to known proteins (APC and VHL).

In many cases, the tumour suppressor gene originally identified through genetic studies has been shown to be lost or mutated in some sporadic tumours. This result suggests that regions of chromosomal aberration may signify the position of important tumour suppressor genes involved both in genetic predisposition to cancer and in sporadic cancer.

One of the hallmarks of several tumour suppressor genes characterized to date is that they are deleted at high frequency in certain tumour types. The deletions often involve loss of a single allele, a so-called loss of heterozygosity, but may also involve homozygous deletion of both alleles. For loss of heterozygosity, the remaining allele is presumed to be non-functional, either because of a pre-existing inherited mutation, or because of a secondary sporadic mutation.

The present invention provides a novel tumour suppressor gene that has not previously been characterised.

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively, and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

All references cited, including patents or patent applications are hereby incorporated by reference. No admission is made that any of the references constitute prior art.

As used herein the term "derived from" shall be taken to indicate that a specific integer may be obtained from a particular source albeit not necessarily directly from that source.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout.

SUMMARY OF THE INVENTION

We have identified a novel tumour suppressor factor, referred to herein as HLS-5 and sequenced mouse and human nucleic acid sequences encoding HLS-5. We have also identified a number of proteins that interact with HLS-5, including proteins involved in DNA repair and cell cycle progression. We have shown that the introduction of HLS-5 into human cells results in a reduction in cell growth. We have found that HLS-5 is differentially expressed in leukaemic patients. We have also found that not only is HLS-5 expressed in breast cancer cells, but that a number of the cells have abnormal HLS-5 alleles, as determined by Southern blotting, raising the possibility that a reduction in the amount of HLS5 due to damage to only one allele (haploinsufficiency) may be linked to carcinogenesis.

Accordingly the present invention provides a polynucleotide encoding an HLS-5 tumour suppressor factor or a homologue thereof.

The present invention also provides a polynucleotide selected from:
(a) polynucleotides comprising the nucleotide sequence set out in SEQ ID No. 1 or SEQ ID No. 3, or a fragment thereof;
(b) polynucleotides comprising a nucleotide sequence capable of hybridising selectively to the nucleotide sequence set out in SEQ ID No. 1 or SEQ ID No. 3, or a fragment thereof.
(c) polynucleotides comprising a polynucleotide sequence which is degenerate as a result of the genetic code to the polynucleotides defined in (a), (b) or (c).
(d) polynucleotides complementary to the polynucleotides of (a) or (b);
with the proviso that the nucleotide sequences set out in SEQ ID No: 3 and SEQ ID No: 5 are specifically excluded.

The present invention also provides a polypeptide which comprises the sequence set out in SEQ ID Nos. 2 or 4 or a polypeptide substantially homologous thereto, or a fragment of the polypeptide of SEQ ID Nos. 2 or 4, with the proviso that a polypeptide consisting of the amino acid sequence shown in SEQ ID No. 4 is specifically excluded. Also provided is a polynucleotide encoding an HLS-5 polypeptide or a homologue or fragment thereof.

The present invention also provides a vector comprising a polynucleotide of the invention, for example an expression vector comprising a polynucleotide of the invention, operably linked to regulatory sequences capable of directing expression of said polynucleotide in a host cell.

The present invention further provides methods of preparing a polynucleotide of the invention comprising polymerising HLS-5 nucleotides to yield a sequence comprised of at least 8 consecutive nucleotides of the HLS-5 gene, preferably at least 15 or 20; and methods of preparing a polypeptide comprising polymerizing amino acids to yield a sequence comprising at least 5 amino acids, preferably at least 8 or 10, encoded within the HLS-5 gene.

The present invention also provides a means to prepare isolated antibodies, which specifically bind to a polypeptide comprised of at least 5 amino acid residues encoded by the HLS-5 gene. Thus, in another aspect, the present invention provides an antibody capable of binding specifically a polypeptide of the invention.

The present invention further provides a method for detecting the presence or absence of a polynucleotide of the invention in a biological sample containing nucleic acid which method comprises:
(a) bringing the biological sample into contact with a polynucleotide probe or primer comprising a polynucleotide of the invention under suitable hybridising conditions; and
(b) detecting any duplex formed between the probe or primer and nucleic acid in the sample.

The present invention also provides a method of detecting a polypeptide of the invention present in biological samples which comprises:
(a) providing an antibody of the invention;
(b) incubating a biological sample with said antibody under conditions which allow for the formation of an antibody-antigen complex; and
(c) determining whether an antibody-antigen complex comprising said antibody is formed.

The present invention further provides a polynucleotide, polypeptide and/or antibody of the invention for use in therapy. Also provides is a method of treating a condition characterised by aberrant cell growth which method comprises administering to a patient in need of treatment an effective amount of a polynucleotide, polypeptide or antibody of the invention.

HLS-5 polypeptides of the invention may also be used in methods of identifying substances capable of affecting HLS-5 function, such as substances capable of modulating cell growth. A substance identified by these methods may be used in a method of modulating cell growth.

Since HLS-5 has been shown to be differentially expressed in leukaemias, and a number of breast cancer cells have been showed to have an altered HLS-5 allele, mutations that interfere with the function of the HLS-5 protein may be involved in the pathogenesis of cancer. Thus, the presence of an altered (or a mutant) HLS-5 gene that leads to altered expression, typically decrease expression, of the HLS-5 gene product or which produces a protein having a loss of function, or altered function, may result in an increased risk of cancer, particularly those cancers mentioned above.

Thus, in one embodiment of the invention there is provided a method for identifying mutations in the HLS-5 alleles of a patient, which method comprises comparing a nucleic acid sequence comprising all or part of an HLS-5 allele derived from a biological sample taken from said patient with the corresponding nucleic acid sequence of a wild type HLS-5 gene and identifying any differences. Such a method may typically be used in a method of identifying a cancerous condition or a predisposition to a cancerous condition in which HLS-5 is implicated.

In a particular embodiment, there is provided a method for screening the HLS-5 gene to identify mutations such as those that cause haploinsufficiency. To detect haploinsufficient HLS-5 gene mutations, a biological sample is preferably prepared and analysed for a difference between the sequence of the HLS-5 gene being analysed and the sequence of the wild-type HLS-5 gene. Mutant HLS-5 genes can be identified by any of the techniques described herein. The mutant alleles can then be sequenced to identify the specific mutation of the particular mutant allele.

Alternatively, mutant HLS-5 genes can be identified by detecting mutant (altered) HLS-5 proteins, using conventional techniques. The mutant genes are then sequenced to identify the specific mutation for each gene. The mutations, especially those that lead to an altered function of the HLS-5 protein, may then be used for the diagnostic and prognostic methods of the present invention.

The present invention also provides kits for screening patients that might be susceptible to cancer, particularly leukaemia and or breast cancer, which ailments are linked to mutations in one or both HLS-5 alleles, for example a mutation resulting in haploinsufficiency of the HLS-5 gene, which kits comprise at least a polynucleotide complementary to the portion of the HLS-5 gene packaged in a suitable container, and instructions for its use to identify the HLS-5, which instructions also include a sequence listing of the complete or a substantially complete HLS-5 gene sequence that is capably of encoding a functional HLS-5 polypeptide sequence in a patient that is not suffering from the specified ailments.

The present invention also provides kits for screening patients to confirm and or identify that they are afflicted with leukaemia and or breast cancer which ailments are linked to haploinsufficiency of the HLS-5 gene, which kits comprise at least a polynucleotide complementary to the portion of the HLS-5 gene packaged in a suitable container, and instructions for its use to identify the HLS-5, which instructions also include a sequence listing of the complete or a substantially complete HLS-5 gene sequence that is capably of encoding a functional HLS-5 polypeptide sequence in a patient that is not suffering from the specified ailments.

In addition, the present invention provides methods of screening drugs for HLS-5 gene therapy to identify suitable drugs for restoring HLS-5 gene product function.

The present invention also provides the means necessary for production of gene-based therapies directed at HLS-5 genes in cells. These therapeutic agents may take the form of polynucleotides comprising all or a portion of the HLS-5 gene placed in appropriate vectors or delivered to target cells in more direct ways such that the function of the HLS-5 gene protein is reconstituted. Therapeutic agents may also take the form of polypeptides based on either a portion of, or the entire protein sequence of HLS-5 gene. These may functionally replace the activity of HLS-5 gene in vivo.

In a further aspect, the present invention provides a method of regulating the growth of a cell which method comprises administering an HLS-5 polypeptide or polynucleotide encoding HLS-5 to said cells. For example, the method of the invention may be used to suppress the growth of abnormally proliferating cells, such as tumour cells as a means to treat neoplastic growths in a patient.

The HLS-5 gene sequences and proteins described herein may be used in diagnostic/prognostic, therapeutic and drug screening methods described herein for the species from which they have been isolated. Further, probes and primers based on the HLS-5 gene sequences disclosed herein may be used to identify homologous HLS-5 gene sequences and proteins in other species.

DETAILED DESCRIPTION OF THE INVENTION

The present invention relates to the identification of a nucleic acid sequence, termed herein HLS-5, as well as the protein and amino acid sequences, including variations thereof which exhibit tumour suppressor activities in acute myeloid leukaemia and breast cancer cells.

The tumor suppressor gene HLS-5 was isolated when J2E cells acquired a monoblastoid phenotype and Epo induced erythroid differentiation was blocked. Cloning and sequencing of a full-length cDNA encoding HLS-5 has revealed it to be a member of the ring finger B-box coiled-coil (RBCC) family of transcriptional regulators. The human homologue of HLS-5 localises to a region of chromosome 8 (8p21.1) that is postulated to harbour one or more tumour suppressor genes specifically associated with breast and prostate carcinomas. This gene sequence is also potentially involved in a chromosomal translocation t(8;17)(p21;q21) associated with acute promyelocytic leukemia (APL). It is postulated that HLS-5 may also be a variant of the t(15;17)(q21;q21) which generates the PML-RAR alpha fusion protein and also results in APL.

RT-PCR analysis has revealed that HLS-5 displays a restricted expression pattern in leukaemias. Moreover, HLS-5 has been found by in situ hybridisation to be expressed in regions of the developing embryo that were actively undergoing apoptosis. The combination of structural homology to known tumour suppressor genes, localisation to a hotspot associated with several types of solid tumours, as well as several cases of leukaemia, indicates that HLS-5 is most likely a candidate tumour suppressor gene located on the short arm of chromosome 8. Additional support for a tumour suppressor role of HLS-5 is the interaction of the molecule with the T:G mismatch-specific thymine-DNA glycosylase and enzymes involved in the ubiquitination pathway, particularly ubiquitin conjugating enzyme 9 (UBC9) which has been shown to be involved in the degradation of key nuclear proteins involved in cell cycle progression and which itself interacts with a number of proteins involved in cell cycle progression and DNA repair (such as transcription factor ETS-1 and topoisomerase II). These molecules have also been shown to interact with p53, a known tumour suppression gene.

A. HLS-5 Polynucleotides

According to the invention there is provided an isolated HLS-5 nucleic acid molecule which molecule typically encodes an HLS-5 polypeptide, allelic variant, or analog, including fragments, thereof. Specifically provided are DNA molecules for use in screening for mutations in an HLS-5 gene and DNA molecules for securing expression of an HLS-5 polypeptide having the biological activity of tumour suppression in a mammal, and selected from the group consisting of: (a) DNA molecules set out in SEQ ID NOS: 1 and 3 or fragments thereof; (b) DNA molecules that hybridize to the DNA molecules defined in (a) or hybridisable fragments thereof; and (c) DNA molecules that code on expression for the amino acid sequence encoded by any of the foregoing DNA molecules.

Preferred DNA molecules according to the invention include DNA molecules comprising the sequence set out in SEQ ID NOS: 1 and 3 or fragments thereof.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

"HLS-5 Allele" refers to normal alleles of the HLS-5 gene sequence as well as alleles carrying variations that predispose individuals to develop cancer of many sites including, for example, leukaemia, breast, ovarian and prostate cancer. Such predisposing alleles are also called "HLS-5 susceptibility alleles".

"HLS-5 gene sequence," "HLS-5 gene," "HLS-5 nucleic acids" or "HLS-5 polynucleotide" each refer to polynucleotides that are likely to be expressed in normal tissue, certain alleles of which predispose an individual to develop leukaemia, breast, ovarian and prostate cancers. Mutations at the HLS-5 gene sequence may be involved in the initiation and/or progression of other types of tumours. The gene sequence is indicated in part by mutations that predispose individuals to develop cancer.

The HLS-5 gene sequence is intended to include coding sequences, intervening sequences and regulatory elements controlling transcription and/or translation. The HLS-5 gene sequence is intended to include all allelic variations of the DNA sequence.

These terms, when applied to a nucleic acid, refer to a nucleic acid that encodes a HLS-5 polypeptide, fragment, homologue or variant, including, e.g., protein fusions or deletions. The nucleic acids of the present invention will possess a sequence that is either derived from, or substantially similar to a natural HLS-5 encoding gene or one having substantial homology with a natural HLS-5 encoding gene or a portion thereof. The coding sequence for murine HLS-5 polypeptide is shown in SEQ ID NO: 1, with the amino acid sequence shown in SEQ ID NO: 2. The coding sequence for human HLS-5 polypeptide is shown in SEQ ID NO: 3 and SEQ ID NO: 7, with the amino acid sequence shown in SEQ ID NO: 4 and SEQ ID NO: 8.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program described below. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, 300, 500 or 1000 nucleotides with the nucleotides sequences set out in SEQ ID. Nos 1 or 3. In particular, homology should typically be considered with respect to those regions of the sequence that encode contiguous amino acid sequences known to be essential for the function of the protein rather than non-essential neighbouring sequences. Thus, for example, homology comparisons are preferrably made over regions corresponding to the Ring finger, B box, coiled coil and/or SPRY domains of the HLS-5 amino acid sequence set out in SEQ ID NOS: 2, 4 or 8 (see the section on HLS-5 polypeptides below). Preferred polypeptides of the invention comprise a contiguous sequence having greater than 50, 60 or 70% homology, more preferably greater than 80, 90, 95 or 97% homology, to one or more of the nucleotides sequences of SEQ ID NO: 1 which encode amino acids 111 to 152, 219 to 266 or 368 to 507 of SEQ ID NO:2 or the equivalent nucleotide sequences in SEQ ID NO: 3. Preferred polynucleotides may alternatively or in addition comprise a contiguous sequence having greater than 80, 90, 95 or 97% homology to the sequence of SEQ ID NO: 1 that encodes amino acids 36 to 75 of SEQ ID NO:2 or the corresponding nucleotide sequences of SEQ ID NO:3

Other preferred polynucleotides comprise a contiguous sequence having greater than 40, 50, 60, or 70% homology, more preferably greater than 80, 90, 95 or 97% homology to the sequence of SEQ ID NO: 1 that encodes amino acids 1 to 35, 76 to 110, 153 to 218 and/or 267 to 367 of SEQ ID No: 2 or the corresponding nucleotide sequences of SEQ ID NO: 3.

Nucleotide sequences are preferably at least 15 nucleotides in length, more preferably at least 20, 30, 40, 50, 100 or 200 nucleotides in length.

Generally, the shorter the length of the polynucleotide, the greater the homology required to obtain selective hybridization. Consequently, where a polynucleotide of the invention consists of less than about 30 nucleotides, it is preferred that the % identity is greater than 75%, preferably greater than 90% or 95% compared with the HLS-5 nucleotide sequences set out in the sequence listings herein. Conversely, where a polynucleotide of the invention consists of, for example, greater than 50 or 100 nucleotides, the % identity compared with the HLS-5 nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 degrees C., typically in excess of 37 degrees C., and preferably in excess of 45 degrees C. Stringent salt conditions will ordinarily be less than 1000 mM, typically less than 500 mM, and preferably less than 200 mM. However, the combination of parameters is much more important than the measure of any single parameter. An example of stringent hybridization conditions is 65° C. and 0.1×SSC (1×SSC=0.15 M NaCl, 0.015 M sodium citrate pH 7.0).

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions.

Such molecules are known in the art and include, for example, those in which peptide linkages substitute for phosphate linkages in the backbone of the molecule.

The present invention provides recombinant nucleic acids comprising all or part of the HLS-5 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

A "Recombinant nucleic acid" is a nucleic acid that is not naturally occurring, or which is made by the artificial combination of two otherwise separated segments of sequence. This artificial combination is often accomplished by either chemical syntheses means, or by the artificial manipulation of isolated segments of nucleic acids, by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source that is abundant in mRNA for the desired proteins. Phage libraries are normally preferred, but other types of libraries may be used. Clones of a library are spread onto plates, transferred to a substrate for screening, denatured and probed for the presence of desired sequences.

The nucleic acid sequences used in this invention will usually comprise at least about five codons (15 nucleotides), more usually at least about 7-15 codons, and most preferably, at least about 35 codons. One or more introns may also be present. This number of nucleotides is usually about the minimal length required for a successful probe that would hybridize specifically with an HLS-5-encoding sequence.

Techniques for nucleic acid manipulation are described generally, for example, in Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kingston, R. E., Moore, D. D., Seidman, J. G., Smith, J. G. and Struhl, K. (1987). John Wiley and Sons, NY. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the terms "HLS-5 gene sequence," and "HLS-5 allele" refer to the double-stranded DNA comprising the gene sequence, allele, or region, as well as either of the single-stranded DNAs comprising the gene sequence, allele or region (i.e. either of the coding and non-coding strands).

As used herein, a "portion" of the HLS-5 gene sequence or region or allele is defined as having a minimal size of at least about eight nucleotides, or preferably about 15 nucleotides, or more preferably at least about 25 nucleotides, and may have a minimal size of at least about 40 nucleotides.

Probe sequences may also hybridize specifically to duplex DNA under certain conditions to form triplex or other higher order DNA complexes. The preparation of such probes and suitable hybridisation conditions are well known in the art.

Detectably labeled nucleic acid molecules hybridisable to a DNA molecule of the invention are also provided and include nucleic acid molecules hybridisable to a non-coding region of an HLS-5 nucleic acid, which non-coding region is selected from the group consisting of an intron, a 5' non-coding region, and a 3' non-coding region. The present invention also provides oligonucleotide primers for amplifying human genomic DNA encoding an HLS-5 polypeptide such as oligonucleotides set out in the Examples (ie HLS-5-1 (GAAACACAAGAGCCGAAAACGC) (SEQ ID NO:9) and HLS-5-2 (AAGCCTGAGCGTGTATCATGGTAGCAGC) (SEQ ID NO:10).

"Probes". Polynucleotide polymorphisms associated with HLS-5 alleles which predispose to certain cancers or are associated with most cancers are detected by hybridisation with a polynucleotide probe which forms a stable hybrid with that of the target sequence, under stringent to moderately stringent hybridisation and wash conditions. If it is expected that the probes will be perfectly complementary to the target sequence, stringent conditions will be used. Hybridisation stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms as well as mutations, these indications need further analysis to demonstrate detection of a HLS-5 susceptibility allele.

Probes for HLS-5 alleles may be derived from the sequences of the HLS-5 region or its cDNAs. The probes may be of any suitable length, which span all or a portion of the HLS-5 region, and which allow specific hybridisation to the HLS-5 region. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe may be employed which hybridises to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kngston, R. E., Moore, D. D., Seidman, J. G., Smith, J. G. and Struhl, K. (1987). John Wiley and Sons, NY. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding HLS-5 are preferred as probes. The probes may also be used to determine whether mRNA encoding HLS-5 is present in a cell or tissue and whether the genomic organisation of the HLS5 locus (8p21) is deleted or otherwise damaged.

A variety of DNA technologies may thus be used to identify mutant alleles in a range of individuals. A number of these alleles may comprise minor alterations to the genomic sequence, such as point mutations including insertions deletions and/or substitutions. Fragments of nucleic acid which comprise these mutations may be used in diagnostic screening as described below. Accordingly, the present invention provides one or more HLS-5 polynucleotides or fragments thereof comprising mutations with respect to the wild type sequence, such as the sequence shown in SEQ ID No. 3. In a further embodiment, the present invention provides a plurality of HLS-5 polynucleotides or fragments thereof for use in screening the DNA of an individual for the presence of one or more mutations/polymorphisms. The plurality of sequences is conveniently provided immobilized to a solid substrate as is described below.

Nucleic Acid Arrays—"DNA Chip" Technology

Polynucleotides of the invention, including probes that may be used to detect both normal (wild type) and abnormal HLS-5 sequences in nucleic acid samples taken from patients, may be immobilized to a solid phase support. The probes for HLS-5 will typically form part of a library of DNA molecules that may be used to detect simultaneously a number of different genes in a given genome.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which may be used to produced the immobilised DNA libraries of the present invention. U.S. Pat. No. 5,837, 832 also provides references for earlier techniques that may also be used. Thus nucleic acid probes may be synthesised in situ on the surface of the substrate.

Alternatively, single-stranded molecules may be synthesised off the solid substrate and each pre-formed sequence applied to a discrete position on the solid substrate. For example, nucleic acids may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10000 to 40000 $cm^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the nucleic acid sequences to the substrate may be by covalent or non-covalent means. The nucleic acid sequences may be attached to the substrate via a layer of molecules to which the library sequences bind. For example, the nucleic acid sequences may be labelled with biotin and the substrate coated with avidin and/or streptavidin. A convenient feature of using biotinylated nucleic acid sequences is that the efficiency of coupling to the solid substrate can be determined easily. Since the nucleic acid sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary nucleic acid sequence to the immobilised nucleic acid library may be determined by a variety of means such as changes in the optical characteristics of the bound nucleic acid (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (SPR)—see WO97/49989, incorporated herein by reference.

Thus the present invention provides a solid substrate having immobilized thereon at least one polynucleotide of the present invention, preferably two or more different polynucleotides of the present invention, for example two or more different HLS-5 polynucleotides corresponding to different alleles. In a preferred embodiment the solid substrate further comprises polynucleotides derived from genes other than the HLS-5 gene.

Preparation of Recombinant or Chemically Synthesised HLS-5 Nucleic Acids; Vectors, Transformation, Host Cells Any HLS-5 nucleic acid specimen, in purified or non-purified form, can be utilised as the starting nucleic acid or acids.

PCR is one such process that may be used to amplify HLS-5 gene sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilised.

The specific nucleic acid sequence to be amplified, i.e., the polymorphic gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in Molecular Cloning: A Laboratory Manual, Cold Spring Harbor, N.Y., p 280-281, 1982). If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP are added to the synthesis mixture, either separately or together with the primers, in adequate amounts and the resulting solution is heated to about 90 degrees-100 degrees C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions.

Thus, for example, if DNA polymerase is used as the agent, the temperature is generally no greater than about 40 degree C. Most conveniently the reaction occurs at room temperature.

Allele specific oligonucleotide primers derived from HLS-5 gene sequence may be useful in determining whether a subject is at risk of suffering from the ailments described herein. Primers direct amplification of a target polynucleotide (eg HLS-5) prior to sequencing. Primers used in any diagnostic assays derived from the present invention should be of sufficient length and appropriate sequence to provide initiation of polymerisation. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of HLS-5 extension products in the presence of the inducing agent for polymerization. The exact length of a primer will depend on many factors, including temperature, buffer, and nucleotide composition. Oligonucleotide primers will typically contain 12-20 or more nucleotides, although they may contain fewer nucleotides.

Primers that may be used in diagnostic assays derived from the present invention should be designed to be substantially complementary to each strand of the HLS-5 genomic gene sequence. This means that the primers must be sufficiently complementary to hybridise with their respective strands under conditions that allow the agent for polymerisation to perform. In other words, the primers should have sufficient complementarity with the 5' and 3' sequences flanking the mutation to hybridise therewith and permit amplification of the HLS-5 genomic gene sequence.

Oligonucleotide primers of the invention employed in the PCR amplification process that is an enzymatic chain reaction that produces exponential quantities of HLS-5 gene sequence relative to the number of reaction steps involved. Typically, one primer will be complementary to the negative (−) strand of the HLS-5 gene sequence and the other is complementary to the positive (+) strand. Annealing the primers to denatured nucleic acid followed by extension with an enzyme, such as the large fragment of DNA polymerase I (Klenow) and nucleotides, results in newly synthesised + and − strands containing the target HLS-5 gene sequence. Because these newly synthesized sequences are also templates, repeated cycles of denaturing, primer annealing, and extension results in exponential production of the region (i.e., the HLS-5 gene sequence) defined by the primers. The product of the chain reaction is a discreet nucleic acid duplex with termini corresponding to the ends of the specific primers employed.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, 1981. One method for synthesising oligonucleotides on a modified solid support is described in U.S. Pat. No. 4,458,066.

The agent for polymerisation may be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (ie, those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each HLS-5 gene sequence nucleic acid strand. Generally, the synthesis will be initiated at the 3' end of each primer and proceed in the 5' direction along the template strand, until synthesis terminates, producing molecules of different lengths.

The newly synthesised HLS-5 strand and its complementary nucleic acid strand will form a double-stranded molecule under hybridizing conditions described above and this hybrid is used in subsequent steps of the process. In the next step, the newly synthesized HLS-5 double-stranded molecule is subjected to denaturing conditions using any of the procedures described above to provide single-stranded molecules.

The steps of denaturing, annealing, and extension product synthesis can be repeated as often as needed to amplify the target polymorphic gene sequence nucleic acid sequence to the extent necessary for detection. The amount of the specific nucleic acid sequence produced will accumulate in an exponential fashion.

Amplification is described in PCR. A Practical Approach, ILR Press, Eds. M. J. McPherson, P. Quirke, and G. R. Taylor, 1992.

The HLS-5 amplification products may be detected by Southern blots analysis, without using radioactive probes. In such a process, for example, a small sample of DNA containing a very low level of the nucleic acid sequence of the HLS-5 gene sequence is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, as described herein.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., Bio/Technology, 3:1008-1012, 1985), allele-specific oligonucleotide (ASO) probe analysis (Conner, et. al., Proc. Natl. Acad. Sci. U.S.A., 80:278, 1983), oligonucleotide ligation assays (OLAs) (Landgren, et. al., Science, 241:1007, 1988), and the like. Molecular techniques for DNA analysis have been reviewed (Landgren, et. al., Science, 242:229-237, 1988).

Preferably, the method of amplifying HLS-5 is by PCR, as described herein and as is commonly used by those of ordinary skill in the art. Alternative methods of amplification have been described and can also be employed as long as the HLS-5 gene sequence amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end that binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37 degrees C. Unlike PCR and LCR, SDA does not require instrumented temperature cycling. Another amplification system useful in the method of the invention is the QB Replicase System. Although PCR is the preferred method of amplification if the invention, these other methods can also be used to amplify the HLS-5 gene sequence as described in the method of the invention.

Large amounts of the polynucleotides of the present invention may also be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eucaryotic cell. Usually the polynucleotide constructs will be suitable for replication in a unicellular host, such as yeast or bacteria, but may also be intended for introduction to (with and without integration within the genome) cultured mammalian or plant or other eucaryotic cell lines.

A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

B. Nucleic Acid Constructs and Vectors

Polynucleotides of the invention may be incorporated into a recombinant replicable vector for introduction into a prokaryotic or eucaryotic host. Such vectors may typically comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native HLS-5 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 supra or Ausubel et al. 1992 supra.

An appropriate promoter and other necessary vector sequences will be selected so as to be functional in the host, and may include, when appropriate, those naturally associated with HLS-5 genes. Examples of workable combinations of cell lines and expression vectors are described in Sambrook et al., 1989 or Ausubel et al., 1992. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukemia virus, mouse tumour virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Thus the present invention provides host cells transformed or transfected with a nucleic acid molecule of the invention. Preferred host cells include bacteria, yeast, mammalian cells, plant cells, insect cells, and human cells in tissue culture. Illustratively, such host cells are selected from the group consisting of *E. coli, Pseudomonas, Bacillus, Streptomyces*, yeast, CHO, R1.1, B-W, L-M, COS 1. COS 7, BSC1, BSC40, BMT10, and Sf9 cells.

Large quantities of the nucleic acids and polypeptides of the present invention may be prepared by expressing the HLS-5 nucleic acids or portions thereof in vectors or other expression vehicles in compatible prokaryotic or eucaryotic host cells. The most commonly used prokaryotic hosts are strains of *Escherichia coli*, although other prokaryotes, such as *Bacillus subtilis* or *Pseudomonas* may also be used.

Also provided are mammalian cells containing an HLS-5 polypeptide encoding DNA sequence and modified in vitro to permit higher expression of HLS-5 polypeptide by means of a homologous recombinational event consisting of inserting an expression regulatory sequence in functional proximity to the HLS-5 polypeptide encoding sequence. The expression regulatory sequence can be an HLS-5 polypeptide expression or not and can replace a mutant HLS-5 polypeptide regulatory sequence in the cell.

Thus, the present invention also provides methods for preparing an HLS-5 polypeptide comprising: (a) culturing a cell as described above under conditions that provide for expression of the HLS-5 polypeptide; and (b) recovering the expressed HLS-5 polypeptide. This procedure can also be accompanied by the steps of: (c) chromatographing the polypeptide using any suitable means known in the art; and (d) purifying the polypeptide by for example gel filtration.

Mammalian or other eucaryotic host cells, such as those of yeast, filamentous fungi, plant, insect, or amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In procaryotic hosts, the transformant may be selected, e.g., by resistance to ampicillin, tetracycline or other antibiotics. Production of a particular product based on temperature sensitivity may also serve as an appropriate marker.

Procaryotic or eucaryotic cells transformed with the polynucleotides of the present invention will be useful not only for the production of the nucleic acids and polypeptides of the present invention, but also, for example, in studying the C. HLS-5 Polypeptides Full length HLS-5 polypeptides of the present invention have about 500 amino acids, encode a tumor suppressor factor in an animal, particularly a mammal, and include allelic variants or homologues. Full length HLS-5 polypeptides also typically comprise a Ring finger motif, a B box, a coiled-coil motif and an SPRY motif (as defined below). HLS-5 polypeptides of the invention also includes fragments and derivatives of full length HLS-5 polypeptides, particularly fragments or derivatives having substantially the same biological activity. The polypeptides can be prepared by recombinant or chemical synthetic methods. Presently preferred HLS-5 polypeptides include those comprising the amino acid sequence of SEQ ID NOS: 2 and 4, or allelic variants or homologues, including fragments, thereof. A particularly preferred polypeptide consists of amino acids 12 to 504 of the amino acid sequence shown as SEQ ID NO: 4 or allelic variants, homologues or fragments, thereof.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. Nos 2, 4 or 8. In particular, homology should typically be considered with respect to those regions of the sequence known to be essential for the function of the protein rather than non-essential neighbouring sequences. Thus, for example, homology comparisons are preferably made over regions corresponding to the Ring finger, B box, coiled coil and/or SPRY domains of the HLS-5 amino acid sequence set out in SEQ ID NOS: 2, 4 or 8. The ring finger corresponds to approximately amino acids 36 to 75 of SEQ ID NO:2. The B box corresponds to approximately amino acids 111 to 152 of SEQ ID NO:2. The coiled coil corresponds to approximately amino acids 219 to 266 of SEQ ID NO:2. The SPRY domain corresponds to approximately amino acids 368 to 507 of SEQ ID NO:2. Preferred polypeptides of the invention comprise a contiguous sequence having greater than 50, 60 or 70% homology, more preferably greater than 80 or 90% homology, to one or more of amino acids 111 to 152, 219 to 266 or 368 to 507 of SEQ ID NO:2 or the corresponding regions of SEQ ID NO:4. Preferred polypeptides may alternatively or in addition comprise a contiguous sequence having greater than 80 or 90% homology, to amino acids 36 to 75 of SEQ ID NO:2 or the corresponding region of SEQ ID NO:4

Other preferred polypeptides comprise a contiguous sequence having greater than 40, 50, 60, or 70% homology, more preferably greater than 80 or 90% homology to amino acids 1 to 35, 76 to 110, 153 to 218 and/or 267 to 367 of SEQ ID No: 2 or the corresponding regions of SEQ ID NO: 4. Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid-Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

HLS-5 polypeptide homologues include those having the amino acid sequences, wherein one or more of the amino acids is substituted with another amino acid which substitutions do not substantially alter the biological activity of the molecule. An HLS-5 polypeptide homologue according to the invention preferably has 80 percent or greater amino acid sequence identity to the human HLS-5 polypeptide amino acid sequence set out in SEQ ID NO: 4. Examples of HLS-5 polypeptide homologues within the scope of the invention include the amino acid sequence of SEQ ID NOS: 4 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

"HLS-5 protein" or "HLS-5 polypeptide" refers to a protein or polypeptide encoded by the HLS-5 gene sequence, variants or fragments thereof. Also included are proteins encoded by DNA that hybridize under high or low stringency conditions, to HLS-5 encoding nucleic acids and closely related polypeptides or proteins retrieved by antisera to the HLS-5 protein(s).

"Protein modifications or fragments" are provided by the present invention for HLS-5 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 supra or Ausubel et al., 1992 supra.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Preferred polypeptides of the invention have substantially similar function to wild type full length HLS-5. Preferred polynucleotides of the invention encode polypeptides having substantially similar function to wild type full length HLS-5. "Substantially similar function" refers to the function of a nucleic acid or polypeptide homologue, variant, derivative or fragment of HLS-5 with reference to the wild-type HLS-5 nucleic acid or wild-type HLS-5 polypeptide.

However, non-functional forms of HLS-5 polypeptides may also be included within the scope of the invention since they may be useful, for example, as antagonists of HLS-5 function.

In addition to the similarity of function, the modified polypeptide may have other useful properties, such as a longer half-life. The similarity of function (activity) of the modified polypeptide may be substantially the same as the activity of the wild-type HLS-5 polypeptide. Alternatively, the similarity of function (activity) of the modified polypeptide may be higher than the activity of the wild-type HLS-5 polypeptide. The function/biological activity of homologues, variant, derivatives or fragments relative to wild type may be determined, for example, by means of biological assays. For example, when administered to HeLa cells, HLS-5 reduces cell growth, resulting in a reduction in colony formation and size. Thus one test for HLS-5 activity is to administer a variant to HeLa cells and determine whether cell growth is inhibited. Preferred homologues, variants and fragments are capable of inhibiting cell growth by a factor of at least 0.5 relative to full length HLS-5, preferably by a factor of at least 0.9. Another test, based on the interaction of HLS-5 with ubiquitin conjugating enzyme (UBC9) and T:G DNA glycosylase, is to determine the extent of binding of a homologue, variant or fragment to UBC9 or T:G DNA glycosylase in an in vitro binding assay. Preferred homologues, variants and fragments are capable of binding to UBC9 or T:G DNA glycosylase by a factor of at least 0.5 relative to full length HLS-5, preferably by a factor of at least 0.9. Suitable in vitro binding assays are well known to skilled persons, such as GST 'pulldown' assays where one component is expressed as a fusion protein linked to glutathione-S-transferase an immobilized on glutathione-sepharose beads.

The modified polypeptide may be synthesised using conventional techniques, or is encoded by a modified nucleic acid and produced using conventional techniques. The modified nucleic acid is prepared by conventional techniques. A nucleic acid with a function substantially similar to the wild-type HLS-5 gene function produces the modified protein described above.

Besides substantially full-length polypeptides, the present invention provides for biologically active fragments of the polypeptides. Significant biological activities include ligand-binding, such as binding to UBC9 and/or T:G DNA glycosylase or other identified interacting molecules, inhibition of cell growth, immunological activity and other biological activities characteristic of HLS-5 polypeptides. Immunological activities include both immunogenic function in a target immune system, as well as sharing of immunological epitopes for binding, serving as either a competitor or substitute antigen for an epitope of the HLS-5 protein.

As used herein, "epitope" refers to an antigenic determinant of a polypeptide. An epitope could comprise three amino acids in a spatial conformation that is unique to the epitope. Generally, an epitope consists of at least five such amino acids, and more usually consists of at least 8-10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for HLS-5 polypeptides or fragments thereof is described below.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The present invention also provides for fusion polypeptides, comprising HLS-5 polypeptides and fragments. Homologous polypeptides may be fusions between two or more HLS-5 polypeptide sequences or between the sequences of HLS-5 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial .beta.-galactosidase, trpE, protein A, .beta.-lactamase, alpha amylase, alcohol dehydrogenase and yeast alpha mating factor.

Fusion proteins will typically be made by either recombinant nucleic acid methods, as described below, or may be chemically synthesized.

"Protein purification" refers to various methods for the isolation of the HLS-5 polypeptides from other biological material, such as from cells transformed with recombinant nucleic acids encoding HLS-5, and are well known in the art. For example, such polypeptides may be purified by immuno-affinity chromatography employing, e.g., the antibodies provided by the present invention. Various methods of protein purification are well known in the art.

The terms "isolated", "substantially pure", and "substantially homogeneous" are used interchangeably to describe a protein or polypeptide that has been separated from components that accompany it in its natural state. A monomeric protein is substantially purified when at least about 60 to 75% of a sample exhibits a single polypeptide sequence. A substantially purified protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for application.

A HLS-5 protein is substantially free of naturally associated components when it is separated from the native contaminants that accompany it in its natural state. Thus, a polypeptide that is chemically synthesised or synthesised in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

D. Diagnosis

Consistent with a number of previously identified tumour suppressor genes, we have shown that the expression of HLS-5 varies in certain tumour types and that the structure of the endogenous HLS-5 gene, as determined by Southern blotting, differs significantly between a number of breast cancer cells, indicating that mutations in HLS-5 may be implicated in certain cancer conditions. Consequently, establishing the HLS-5 status of an individual may be a useful diagnostic and/or prognostic tool.

Diagnostic and prognostic methods will generally be conducted using a biological sample obtained from a patient. A "sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumours, organs, tissue and samples of in vitro cell culture constituents.

According to the diagnostic and prognostic methods of the present invention, alteration of the wild-type HLS-5 gene sequence may be detected using anyone of the methods described herein. In addition, the diagnostic and prognostic methods can be performed to detect the wild-type HLS-5 gene sequence and confirm a lack of a predisposition to cancer at the HLS-5 gene sequence.

As used herein, the terms "diagnosis" or "prognosis," as used in the context of neoplasia, are used to indicate 1) the classification of lesions as neoplasia, 2) the determination of the severity of the neoplasia, or 3) the monitoring of the disease progression, prior to, during and after treatment.

"Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those that occur only in certain tissues, e.g., in the tumour tissue, and are not inherited in the germline. Germline mutations can be found in any of a body's tissues and are inherited. If only a single HLS-5 allele is somatically mutated, an early neoplastic state is indicated. However, if both alleles are somatically mutated, then a late neoplastic state is indicated. The finding of HLS-5 mutations thus provides both diagnostic and prognostic information. A HLS-5 gene sequence that is not deleted (e.g., found on the sister chromosome to a chromosome carrying a HLS-5 deletion) can be screened for other mutations, such as insertions, small deletions, and point mutations.

The predisposition of a patient to cancers, such as leukaemia, breast prostrate and ovarian cancer, and the other cancers identified herein, can be ascertained by testing any tissue of the patient for mutations of the HLS-5 gene. For example, a person who has inherited a germline HLS-5 mutation might be prone to develop the above cancers. Most simply, blood can be drawn and DNA extracted from the cells of the blood. In addition, prenatal diagnosis can be accomplished by testing fetal cells, placental cells or amniotic cells for mutations of the HLS-5 gene. Alteration of a wild-type HLS-5 allele, whether, for example, by point mutation or deletion, can be detected by any of the means discussed herein.

To detect the alteration of the wild-type HLS-5 gene in a tissue, it is helpful to isolate the tissue free from surrounding normal tissues. Means for enriching tissue preparation for tumour cells are known in the art. For example, the tissue may be isolated from paraffin or cryostat sections. Cancer cells may also be separated from normal cells by flow cytometry. These techniques, as well as other techniques for separating tumour cells from normal cells, are well known in the art. If the tumour tissue is highly contaminated with normal cells, detection of mutations is more difficult.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases, tumours, or both. Southern blots displaying hybridising fragments (differing in length from control DNA when probed with sequences near or including the HLS-5 gene sequence) indicate a possible mutation. If restriction enzymes that produce very large restriction fragments are used, then pulsed field gel electrophoresis (PFGE) may also be employed.

Detection of point mutations may also be accomplished by molecular cloning of the HLS-5 allele(s) and sequencing the allele(s) using techniques well known in the art. Alternatively, the gene sequences can be amplified directly from a genomic DNA preparation from the minor tissue, using known techniques. The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

Some other useful diagnostic techniques for detecting the presence of HLS-5 and or mutations to the gene include, but are not limited to: 1) allele-specific PCR; 2) single stranded conformation analysis (SSCA); 3) denaturing gradient gel electrophoresis (DGGE); 4) RNase protection assays; 5) the use of proteins which recognize nucleotide mismatches, such as the *E. coli* mutS protein; 6) allele-specific oligonucleotides (ASOs); and 7) fluorescent in situ hybridisation (FISH). Other approaches based on the detection of mismatches between the two complementary DNA strands include clamped denaturing gel electrophoresis (CDGE), heteroduplex analysis (HA) and chemical mismatch cleavage (CMC).

For allele-specific PCR, primers are used which hybridize at their 3' ends to a particular HLS-5 mutation. If the particular HLS-5 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the HLS-5 mutation found in that individual.

SSCA detects a band which migrates differentially because the sequence change causes a difference in single-strand, intramolecular base pairing. This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation.

DGGE detects differences in migration rates of mutant sequences compared to wild-type sequences, using a denaturing gradient gel.

In the RNase protection method a labeled riboprobe that is complementary to the human wild-type HLS-5 gene coding sequence is used. The riboprobe and either mRNA or DNA isolated from the tumour tissue are hybridised together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the HLS-5 mRNA or gene but can be a segment of either. If the riboprobe comprises only a segment of the HLS-5 mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR (see below) before hybridisation.

In the mutS assay, the protein binds only to sequences that contain a nucleotide mismatch in a heteroduplex between mutant and wild-type sequences.

Once a mutation is known, a gene specific detection approach such as allele specific oligonucleotide (ASO) hybridisation can be utilised to rapidly screen large numbers of samples for that same mutation. In an allele-specific oligonucleotide assay, an oligonucleotide is designed which detects a specific sequence which contains a region of the HLS-5 gene sequence harboring a known mutation, and the assay is performed by detecting the presence or absence of a hybridisation signal. For example, one oligomer may be about 30 nucleotides in length, corresponding to a portion of the HLS-5 gene sequence. By use of a battery of such allele-specific probes, PCR amplification products can be screened to identify the presence of a previously identified mutation in the HLS-5 gene. Hybridisation of allele-specific probes with amplified HLS-5 sequences can be performed, for example, on a nylon filter. Hybridisation to a particular probe under stringent hybridisation conditions indicates the presence of the same mutation in the tumour tissue as in the allele-specific probe.

In addition to the above methods HLS-5 genes and mutants thereof may be detected using conventional probe technology. When probes are used to detect the presence of the target sequences (for example, in screening for cancer susceptibility), the biological sample to be analysed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the sample nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample nucleic acid and probe are incubated under conditions that promote stable hybrid formation of the target sequence in the probe with the putative targeted sequence in the sample. The region of the probes that is used to bind to the sample can be made completely complementary to the targeted region of the human chromosomal location for HLS-5. Therefore, high stringency conditions are desirable in order to prevent false positives. However, conditions of high stringency may be used only if the probes are complementary to regions of the chromosome that are unique in the genome. The stringency of hybridisation is determined by a number of factors during hybridisation and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand that is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety.

Two detection methodologies that are particularly effective, work on the principle that a small ligand (such as digoxigenin, biotin, or the like) is attached to a nucleic acid probe capable of specifically binding HLS-5. The small ligand is then detected. In one example, the small ligand attached to the nucleic acid probe might be specifically recognized by an antibody-enzyme conjugate. For example, digoxigenin may be attached to the nucleic acid probe. Hybridisation is then detected by an antibody-alkaline phosphatase conjugate that turns over a chemiluminescent substrate. In a second example, the small ligand may be recognized by a second ligand-enzyme conjugate that is capable of specifically complexing to the first ligand. A well-known example is the biotin-avidin type of interactions.

It is also contemplated within the scope of this invention that the nucleic acid probe assays of this invention will employ a cocktail of nucleic acid probes capable of detecting HLS-5. Thus, in one example to detect the presence of HLS-5 in a cell sample, more than one probe complementary to HLS-5 is employed and in particular the number of different probes is alternatively 2, 3, or 5 different nucleic acid probe sequences. In another example, to detect the presence of mutations in the HLS-5 gene sequence in a patient, more than one probe complementary to HLS-5 is employed where the cocktail includes probes capable of binding to the allele-specific mutations identified in populations of patients with alterations in HLS-5. In this embodiment, any number of probes can be used, and will preferably include probes corresponding to the major gene mutations identified as predisposing an individual to the cancerous states described herein.

In a highly preferred embodiment, screening techniques based on hybridization to probes, particularly a plurality of probes that correspond to allele-specific mutations use probes immobilized to solid substrates as described above, for example in the form of DNA arrays on silicon substrates (DNA chips).

Alteration of wild-type HLS-5 genes can also be detected by screening for alteration of wild-type HLS-5 protein. Such alterations can be determined by amino acid sequence analysis in accordance with conventional techniques. More preferably, antibodies (polyclonal or monoclonal) may be used to detect differences in, or the absence of HLS-5 proteins or peptides. The antibodies may be prepared as discussed below under the heading "Antibodies". For example, monoclonal antibodies immunoreactive with HLS-5 can be used to screen a tissue. Lack of cognate antigen would indicate a HLS-5 mutation. Antibodies specific for products of mutant alleles could also be used to detect mutant HLS-5 gene product. Such immunological assays can be done in any convenient format known in the art. These include Western blots, immunohistochemical assays and ELISA assays. Any means for detecting an altered HLS-5 protein can be used to detect alteration of wild-type HLS-5 genes. Functional assays, such as protein binding determinations, can be used. In addition, assays can be used which detect HLS-5 biochemical function. Finding a mutant HLS-5 gene product indicates alteration of a wild-type HLS-5 gene.

In a preferred embodiment of the invention, antibodies will immunoprecipitate HLS-5 proteins from solution as well as react with HLS-5 protein on Western or immunoblots of polyacrylamide gels. In another preferred embodiment, antibodies will detect HLS-5 proteins in paraffin or frozen tissue sections, using immunocytochemical techniques.

Preferred embodiments relating to methods for detecting HLS-5 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

E. Antibodies

The present invention also provides labeled and unlabeled monoclonal and polyclonal antibodies specific for HLS-5 polypeptides of the invention and immortal cell lines that produce a monoclonal antibody of the invention. Antibody preparation according to the invention involves: (a) conjugating an HLS-5 polypeptide to a carrier protein; (b) immunizing a host animal with the HLS-5 polypeptide fragment-carrier protein conjugate of step (a) admixed with an adjuvant; and (c) obtaining antibody from the immunized host animal.

According to the invention, HLS-5 polypeptide produced recombinantly or by chemical synthesis, and fragments or other derivatives or analogs thereof, including fusion proteins, may be used as an immunogen to generate antibodies that recognize the HLS-5 polypeptide. Such antibodies include but are not limited to polyclonal, monoclonal, chimeric, single chain, Fab fragments, and an Fab expression library.

Thus, the present invention also provides polyclonal and/or monoclonal antibodies and fragments thereof, and immunologic binding equivalents thereof, which are capable of specifically binding to the HLS-5 polypeptides and fragments thereof or to polynucleotide sequences from the HLS-5 region, particularly from the HLS-gene sequence or a portion thereof. Such antibodies thus include for example, but are not limited to polyclonal, monoclonal, chimeric, single chain, Fab fragments, and an Fab expression library. Production of antibodies specific for HLS-5 polypeptides or fragments thereof is described below.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to HLS-5 polypeptide, or fragment, derivative or analog thereof. For the production of antibody, various host animals can be immunized by injection with the HLS-5 polypeptide, or a derivative (e.g., fragment or fusion protein) thereof, including but not limited to rabbits, mice, rats, sheep, goats, etc. In one embodiment, the HLS-5 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HLS-5 polypeptide, or fragment, analog, or derivative thereof, any technique that provides for the production of antibody molecules by continuous cell lines in culture may be used. These include but are not limited to the hybridoma technique originally developed by Kohler et al., *Nature*, 256: 495-497 (1975), as well as the trioma technique, the human B-cell hybridoma technique [Kozbor et al., *Immunology Today*, 4:72 (1983)], and the EBV-hybridoma technique to produce human monoclonal antibodies [Cole et al., in *Monoclonal Antibodies and Cancer Therapy*, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilizing recent technology (PCT/US90/02545). According to the invention, human antibodies may be used and can be obtained by using human hybridomas [Cote et al., *Proc. Natl. Acad. Sci. USA*, 80:2026-2030 (1983)] or by transforming human B cells with EBV virus in vitro (Cole et al., 1985, supra). In fact, according to the invention, techniques developed for the production of "chimeric antibodies" [Morrison et al., *J. Bacteriol.*, 159-870 (1984); Neuberger et al., *Nature*, 312:604-608 (1984); Takeda et al., *Nature*, 314:452-454 (1985)] by splicing the genes from a mouse antibody molecule specific for an HLS-5 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce HLS-5 polypeptide-specific single chain antibodies. An additional embodiment of the invention utilizes the techniques described for the construction of Fab expression libraries [Huse et al., *Science*, 246: 1275-1281 (1989)] to allow rapid and easy identification of monoclonal Fab fragments with the desired specificity for an HLS-5 polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies that recognize a specific epitope of an HLS-5 polypeptide, one may assay generated hybridomas for a product that binds to an HLS-5 polypeptide fragment containing such epitope. For selection of an antibody specific to an HLS-5 polypeptide from a particular species of animal, one can select on the basis of positive binding with HLS-5 polypeptide expressed by or isolated from cells of that species of animal.

The foregoing antibodies can be used in methods known in the art relating to the localization and activity of the HLS-5 polypeptide, e.g., for Western blotting, imaging HLS-5 polypeptide in situ, measuring levels thereof in appropriate physiological samples, etc.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the pGEX vector can be used to express the polypeptide (Smith et al., 1988, supra). Alternatively, one can use only hydrophilic domains to generate the fusion protein. The expressed protein will be prepared in quantity and used to immunize rabbits in Freunds adjuvant.

In yet another embodiment, recombinant HLS-5 polypeptide is used to immunize rabbits, and the polyclonal antibodies are immunopurified prior to further use. The purified antibodies are particularly useful for semi-quantitative assays, particularly for detecting the presence of HLS-5 polypeptide.

Preferably, the anti-modulator antibody used in the diagnostic and therapeutic methods of this invention is an affinity-purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

F. Assays

The present invention provides assays that are suitable for identifying substances that bind to HLS-5 polypeptides (reference to which includes homologues, variants, derivatives and fragments as described above). In addition, assays are provided that are suitable for identifying substances that interfere with HLS-5 binding to cellular components involved in DNA repair and/or cell cycle progression, for example proteins identified in yeast two-hybrid screens as interacting with HLS-5 (such as T:G DNA glycosylase and UBC9). Such assays are typically in vitro. Assays are also provided that test the effects of candidate substances identified in preliminary in vitro assays on intact cells in whole cell assays.

Candidate Substances

A substance that alters cell growth as a result of an interaction with HLS-5 polypeptides may do so in several ways. It may directly disrupt the binding of HLS-5 to a cellular component of the cell cycle machinery by, for example, binding to HLS-5 and masking or altering the site of interaction with the other component. Candidate substances of this type may conveniently be preliminarily screened by in vitro binding assays as, for example, described below and then tested, for example in a whole cell assay as described below. Examples of candidate substances include antibodies which recognise HLS-5.

A substance which can bind directly to HLS-5 may also inhibit its function in cell division by altering its subcellular localisation thus preventing HLS-5 and interacting proteins from coming into contact within the cell. This can be tested using, for example the whole cells assays described below. Non-functional homologues of HLS-5 may also be tested for inhibition of HLS-5 activity since they may compete with HLS-5 for binding to cellular components. Such non-functional homologues may include naturally occurring HLS-5 mutants and modified HLS-5 sequences or fragments thereof. In particular, fragments of HLS-5 which comprise one or more of the ring finger domain, B box, coiled coil domain, SPRY domain or other functional domains but lack at least one functional domains may be used to compete with full length HLS-5.

Alternatively, instead of preventing the association of the components directly, the substance may alter the biologically available amount of HLS-5. This may be by inhibiting expression of the component, for example at the level of transcription, transcript stability, translation or post-translational stability. An example of such a substance would be antisense RNA or double-stranded interfering RNA sequences which suppresses the amount of HLS-5 mRNA biosynthesis. In particular, inhibition of HLS-5 binding to proteins of the ubiquitin-mediated protein degradation pathways, such as UBC9) may increase the amount of available HLS-5 in a cell.

Suitable candidate substances include peptides, especially of from about 5 to 30 or 10 to 25 amino acids in size, based on the sequence of the various domains of HLS-5 described above, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for HLS-5. Furthermore, combinatorial libraries, peptide and peptide mimetics, defined chemical entities, oligonucleotides, and natural product libraries may be screened for activity as regulators of HLS-5 activity. The candidate substances may be used in an initial screen in batches of, for example 10 substances per reaction, and the substances of those batches which show inhibition tested individually. Candidate substances which show activity in in vitro screens such as those described below can then be tested in whole cell systems, such as mammalian cells which will be exposed to the inhibitor and tested for effects on cell growth.

HLS-5 Binding Assays

One type of assay for identifying substances that bind to HLS-5 involves contacting an HLS-5 polypeptide, which is immobilised on a solid support, with a non-immobilised candidate substance determining whether and/or to what extent the HLS-5 polypeptide and candidate substance bind to each other. Alternatively, the candidate substance may be immobilised and the HLS-5 polypeptide non-immobilised.

In a preferred assay method, the HLS-5 polypeptide is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads. As a control, binding of the candidate substance, which is not a GST-fusion protein, to the immobilised HLS-5 polypeptide is determined in the absence of the HLS-5 polypeptide. The binding of the candidate substance to the immobilised HLS-5 polypeptide is then determined. This type of assay is known in the art as a GST pulldown assay. Again, the candidate substance may be immobilised and the HLS-5 polypeptide non-immobilised.

It is also possible to perform this type of assay using different affinity purification systems for immobilising one of the components, for example Ni-NTA agarose and hexahistidine-tagged components.

Binding of the HLS-5 polypeptide to the candidate substance may be determined by a variety of methods well-known in the art. For example, the non-immobilised component may be labelled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 μg/ml, more preferably from 200 to 300 μg/ml.

Another type of in vitro assay involves determining whether a candidate substance modulates binding of a protein known to interact with HLS-5, such as T:G DNA glycosylase. Such an assay typically comprises contacting HLS-5 protein with the known interacting protein in the presence or absence of the candidate substance and determining if the candidate substance has an affect on HLS-5 binding to the known interacting protein.

Whole Cell Assays

Candidate substances may also be tested on whole cells for their effect on cell growth. Preferably the candidate substances have been identified by the above-described in vitro methods. Alternatively, rapid throughput screens for substances capable of inhibiting cell growth, may be used as a preliminary screen and then used in the in vitro assay described above to confirm that the affect is on HLS-5.

The candidate substance, i.e. the test compound, may be administered to the cell in several ways. For example, it may be added directly to the cell culture medium or injected into the cell. Alternatively, in the case of polypeptide candidate substances, the cell may be transfected with a nucleic acid construct which directs expression of the polypeptide in the cell. Preferably, the expression of the polypeptide is under the control of a regulatable promoter.

Typically, an assay to determine the effect of a candidate substance identified by the method of the invention on cell growth comprises administering the candidate substance to a cell and determining whether the substance affects cell growth. The extent of cell growth may be determined using parameters such as the number and sizes of cell colonies. The extent of growth in treated cells is compared with the extent of growth in an untreated control cell population to determine any affect.

The concentration of candidate substances used will typically be such that the final concentration in the cells is similar to that described above for the in vitro assays.

In a preferred embodiment, the candidate substance is administered to the cell together with functional HLS-5. Since HLS-5 has the effect of reducing cell growth, a substance that inhibits HLS-5 may serve to restore cell growth back to the levels seen in the absence of HLS-5. Alternatively, if cell growth is further reduced, then the substance may be an activator of HLS-5 function.

A candidate substance is typically considered to be an inhibitor of HLS-5 function if cell growth is increased by at least 10%, preferably at least 20, 30 or 40% relative to the extent of cell growth seen in the presence of HLS-5 and absence of the candidate substance. By contrast, a candidate substance is typically considered to be an activator of HLS-5 function if cell growth is further decreased by at least 10%, preferably at least 20, 30 or 40% relative to the extent of cell growth seen in the presence of HLS-5 and absence of the candidate substance.

Thus, this invention is also particularly useful for screening compounds by using the HLS-5 polypeptide or binding fragment thereof in any of a variety of drug screening techniques.

The HLS-5 polypeptide or fragment employed in such a test may either be free in solution, affixed to a solid support, or borne on a cell surface. One method of drag screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a HLS-5 polypeptide or fragment and the agent being tested, or examine the degree to which the formation of a complex between a HLS-5 polypeptide or fragment and a known ligand is interfered with by the agent being tested.

Thus, the present invention provides methods of screening for drugs comprising contacting such an agent with a HLS-5 polypeptide or fragment thereof and assaying (i) for the presence of a complex between the agent and the HLS-5 polypeptide or fragment, or (ii) for the presence of a complex between the HLS-5 polypeptide or fragment and a ligand, by methods well known in the art. In such competitive binding assays the HLS-5 polypeptide or fragment is typically labeled. Free HLS-5 polypeptide or fragment is separated from that present in a protein:protein complex, and the amount of free (i.e., uncomplexed) label is a measure of the binding of the agent being tested to HLS-5 or its interference with HLS-5:ligand binding, respectively.

Another technique for drug screening provides high throughput screening for compounds having suitable binding affinity to the HLS-5 polypeptides and is described in detail in Geysen, PCT published application WO 84/03564, published on Sep. 13, 1984. Briefly stated, large numbers of different small peptide test compounds are synthesised on a solid substrate, such as plastic pins or some other surface. The peptide test compounds are reacted with HLS-5 polypeptide and washed. Bound HLS-5 polypeptide is then detected by methods well known in the art.

Purified HLS-5 can be coated directly onto plates for use in the aforementioned drug screening techniques. However, antibodies to the polypeptide can be used to capture antibodies to immobilize the HLS-5 polypeptide on the solid phase.

This invention also contemplates the use of competitive drug screening assays in which antibodies capable of specifically binding the HLS-5 polypeptide compete with a test compound for binding to the HLS-5 polypeptide or fragments thereof. In this manner, the antibodies can be used to detect the presence of any peptide that shares one or more antigenic determinants of the HLS-5 polypeptide.

A further technique for drug screening involves the use of host eucaryotic cell lines or cells (such as described above) that have a nonfunctional HLS-5 gene. These host cell lines or cells are defective at the HLS-5 polypeptide level. The host cell lines or cells are grown in the presence of drug compound. The rate of growth of the host cells is measured to determine if the compound is capable of regulating the growth of HLS-5 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. In one approach, one first determines the three-dimensional structure of a protein of interest (e.g., HLS-5 polypeptide) or, for example, of the HLS-5-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors. In addition, peptides (e.g., HLS-5 polypeptide) are analysed by an alanine scan. In this technique, an amino acid residue is replaced by Ala, and its effect on the peptide's activity is determined. Each of the amino acid residues of the peptide is analysed in this manner to determine the important regions of the peptide.

It is also possible to isolate a target-specific antibody, selected by a functional assay, and then to solve its crystal structure. In principle, this approach yields a pharmacophore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacophore.

Thus, one may design drugs that have, e.g., improved HLS-5 polypeptide activity or stability or which act as inhibitors, agonists, antagonists, etc. of HLS-5 polypeptide activity. By virtue of the availability of cloned HLS-5 sequences, sufficient amounts of the HLS-5 polypeptide may be made available to perform such analytical studies as x-ray crystallography. In addition, the knowledge of the HLS-5 protein sequence provided herein will guide those employing computer modeling techniques in place of, or in addition to x-ray crystallography.

G. Therapeutic Uses

Tumour suppressor factors, as their name suggests, have been shown to play an important role in disease processes such as tumourigenesis. A number of tumour suppressors are known to be intimately involved in regulating cell cycle progression and provide important checks on inappropriate cell division. For example, p53 induces apoptosis in cells subjected to DNA damage cause by UV irradiation. Inactivation of one or more tumour suppressors is generally an important part of tumour progression. Consequently, extensive research effort has been directed to inhibiting tumour progression by reactivating tumour suppressor function to enable the normal cell division checkpoint pathways to trigger cell death of abnormal tumour cells.

One approach is to administer functional tumour suppressor proteins or nucleic acids that direct expression of functional tumour suppressor proteins to tumour cells, a procedure termed gene therapy.

Another approach, particularly in cells where there is haploinsufficiency (i.e. a reduction in the concentration of tumour suppressor factor due to inactivation of one allele) is to administer one or more compounds that enhance the activity of any tumour suppressor factor present in the cell. This could be as a result of either enhancing the amount of tumour suppressor factor (for example by reducing protein turnover or increasing the rate of transcription) or modifying the biological activity of the tumour suppressor, such as increasing its affinity for a target molecule.

Thus the present invention provides a method of reducing or inhibiting cell division in a cell having reduced HLS-5 activity relative to normal cells which method comprises administering to said cell a functional HLS-5 polypeptide or polynucleotide encoding said polypeptide. Preferably said cell is a neoplastic/tumour cell. More preferably said cell is a leukaemia or breast cancer cell. The present invention further provides the use of a polypeptide or polynucleotide of the invention, which polypeptide or polynucleotide is, or encode, biologically active HLS-5 in gene therapy. Also provided is a method of treating a disease characterized by aberrant cell growth, such as abnormally proliferating cells, which method comprises administering to said cells a functional HLS-5 polypeptide or polynucleotide encoding said polypeptide to suppress proliferation in said cells.

Gene Therapy

According to the present invention, a method is also provided of supplying wild-type HLS-5 function to a cell that carries mutant HLS-5 alleles. Supplying such a function should suppress neoplastic growth of the recipient cells. HLS-5 function may be provided either through the use of gene therapy or alternatively it might be provided in the form of protein therapy which therapy is capable of delivering polypeptide over a sustained period of time.

The wild-type HLS-5 gene or a part of the gene may be introduced into the cell in a vector or as naked DNA such that the gene remains extrachromosomal. In such a situation, the gene will be expressed by the cell from the extrachromosomal location. If a gene fragment is introduced and expressed in a cell carrying a mutant HLS-5 allele, the gene fragment should encode a part of the HLS-5 protein that is required for non-neoplastic growth of the cell. More preferred is the situation where the wild-type HLS-5 gene or a part thereof is introduced into the mutant cell in such a way that it recombines with the endogenous mutant HLS-5 gene present in the cell. Such recombination requires a double recombination event that results in the correction of the HLS-5 gene mutation. Vectors for introduction of genes both for recombination and for extrachromosomal maintenance are known in the art, and any suitable vector may be used. However, replication-incompetent retroviral vectors have proved safe and effective in recent trials and most of the approved human gene therapy trials to date rely on retroviral vectors. Thus it is preferred to use retroviral vectors, such as lentiviral vectors, comprising a polynucleotide of the invention and capable of expressing a polypeptide of the invention. Other viral vector systems include adenoviral vectors and herpes virus vectors.

Methods for introducing DNA into cells such as electroporation, calcium phosphate co-precipitation and viral transduction are known in the art, and the choice of method is within the competence of the person skilled in the art. A further gene transfer technique that has been approved by the FDA is the transfer of plasmid DNA in liposomes. Suitable liposome compositions include Lipofectin™.

Cells transformed with the wild-type HLS-5 gene can be used as model systems to study cancer remission and drug treatments that promote such remission.

As generally discussed above, the HLS-5 gene or fragment, where applicable, may be employed in gene therapy methods in order to increase the amount of the expression products of such genes in cancer cells. Such gene therapy is particularly appropriate for use in both cancerous and pre-cancerous cells, in which the level of HLS-5 polypeptide is absent or diminished compared to normal cells. It may also be useful to increase the level of expression of a given HLS-5 gene even in those tumour cells in which the mutant gene is expressed at a "normal" level, but the gene product is not fully functional.

Gene therapy would be carried out according to generally accepted methods. Cells from a patient's tumour would be first analysed by the diagnostic methods described above, to ascertain the production of HLS-5 polypeptide in the tumour cells. A virus or plasmid vector (see further details below), containing a copy of the HLS-5 gene linked to expression control elements and capable of replicating inside the tumour cells, is prepared. Suitable vectors are known, such as disclosed in U.S. Pat. No. 5,252,479 and PCT published application WO 93/07282. The vector is then injected into the patient, either locally at the site of the tumour or systemically (in order to reach any tumour cells that may have metastasized to other sites). If the transfected gene is not permanently incorporated into the genome of each of the targeted tumour cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40, adenovirus, vaccinia virus, adeno-associated virus, herpesviruses including HSV and EBV, and retroviruses of avian, murine, and human origin. Most human gene therapy protocols have been based on disabled murine retroviruses.

Nonviral gene transfer methods known in the art include chemical techniques such as calcium phosphate co-precipitation; mechanical techniques, for example microinjection; membrane fusion-mediated transfer via liposomes; and direct DNA uptake and receptor-mediated DNA transfer. Viral-mediated gene transfer can be combined with direct in vivo gene transfer using liposome delivery, allowing one to direct the viral vectors to the tumour cells and not into the surrounding non-dividing cells. Alternatively, the retroviral vector producer cell line can be injected into tumours. Injection of producer cells would then provide a continuous source of vector particles. This technique has been approved for use in humans with inoperable brain tumours.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumour deposits, for example, following direct in situ administration.

Gene transfer techniques that target DNA directly to breast and ovarian tissues, e.g., epithelial cells of the breast or ovaries, are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include the estrogen receptor and its ligand, estrogen (and estrogen analogues). These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy involves two steps that can be performed singly or jointly. In the first step, prepubescent females who carry a HLS-5 susceptibility allele are treated with a gene delivery vehicle such that some or all of their mammary ductal epithelial precursor cells receive at least one additional copy of a functional normal HLS-5 allele. In this step, the treated individuals have reduced risk of breast cancer to the extent that the effect of the susceptible allele has been countered by the presence of the normal allele. In the second step of a preventive therapy, predisposed young females, in particular women who have received the proposed gene therapeutic treatment, undergo hormonal therapy to mimic the effects on the breast of a full term pregnancy.

Polypeptides that have HLS-5 activity can also be supplied to cells that carry mutant or missing HLS-5 alleles.

Active HLS-5 molecules can be introduced into cells by microinjection or by use of liposomes, for example. Alternatively, some active molecules may be taken up by cells, actively or by diffusion. Extracellular application of the HLS-5 gene product may be sufficient to affect tumour growth. Supply of molecules with HLS-5 activity should lead to partial reversal of the neoplastic state. Other molecules with HLS-5 activity (for example, peptides, drugs or organic compounds) may also be used to effect such a reversal. Modified polypeptides having substantially similar function are also used for protein therapy.

Similarly, cells and animals that carry a mutant HLS-5 allele can be used as model systems to study and test for substances which have potential as therapeutic agents. These may be isolated from individuals with HLS-5 mutations, either somatic or germline. Alternatively, the cell line can be engineered to carry the mutation in the HLS-5 allele, as described above. After a test substance is applied to the cells, the neoplastically transformed phenotype of the cell is determined. Any trait of neoplastically transformed cells can be assessed, including anchorage-independent growth, tumourigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant HLS-5 alleles, usually from a second animal species, as well as insertion of disrupted homologous genes. Alternatively, the endogenous HLS-5 gene(s) of the animals may be disrupted by insertion or deletion mutation or other genetic alterations using conventional techniques. After test substances have been administered to the animals, the growth of tumours must be assessed. If the test substance prevents or suppresses the growth of tumours, then the test substance is a candidate therapeutic agent for the treatment of the cancers identified herein. These animal models provide an extremely important testing vehicle for potential therapeutic products.

Therapeutic Compounds

Compounds identified by the assay methods of the present invention as regulating HLS-5 function may also be used in therapeutic methods of the present invention. For example, a compound identified as binding to and enhancing HLS-5 function may be administered to abnormally proliferating cells that are haploinsufficient for the HLS-5 gene.

H. Administration

Substances identified or identifiable by the assay methods of the invention may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular, oral or transdermal administration. Typically, each substance may be administered at a dose of from 0.01 to 30 mg/kg body weight, preferably from 0.1 to 10 mg/kg, more preferably from 0.1 to 1 mg/kg body weight.

Polynucleotides/vectors encoding polypeptide components (or antisense constructs) for use in therapeutic methods may be administered directly as a naked nucleic acid construct. They may further comprise flanking sequences homologous to the host cell genome. When the polynucleotides/vectors are administered as a naked nucleic acid, the amount of nucleic acid administered may typically be in the range of from 1 μg to 10 mg, preferably from 100 μg to 1 mg. It is particularly preferred to use polynucleotides/vectors that target specifically tumour cells, for example by virtue of suitable regulatory constructs or by the use of targeted viral vectors.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector according to the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration and dosages described are intended only as a guide since a skilled practitioner will be able to determine readily the optimum route of administration and dosage for any particular patient and condition.

BEST MODE(S) FOR CARRYING OUT THE INVENTION

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

Methods of molecular cloning, immunology and protein chemistry which are not explicitly described in the following examples are reported in the literature and are known by those skilled in the art. General texts that described conventional molecular biology, microbiology, and recombinant DNA techniques within the skill of the art, included, for example: Sambrook et al., *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); and Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York.

The examples refer to the following Figures:

DESCRIPTION OF THE DRAWINGS

FIG. 2 illustrates J2E-m2 minus J2E subtraction products. This table summarises the identities of HLS1-HLS8 identified in the RDA procedure as determined by sequence analysis and comparison to the Genbank database. Expression summarises the differential expression of each fragment as determined by Northern blot of mRNA derived from both J2E and J2E-m2 cell lines. nd—not determined.

EXAMPLES cDNA RDA

Poly(A)$^+$RNA was isolated from J2E driver and J2E-m2 tester cell lines (Keil, U., Busfield, S. J., Farr, T. J., Papadimitriou, J., Green, A. R., Begley, C. G. and Klinken, S. P. (1995) Emergence of myeloid cells from cultures of J2E erythroid cells is linked with karyotypic abnormalities. *Cell Growth Differ*, 6, 439-448; Klinken, S. P., Nicola, N. A. and Johnson, G. R. (1988) In vitro-derived leukemic erythroid cell lines generated by a raf- and myc-containing retrovirus differentiate in response to erythropoietin. *Proc Natl Acad Sci USA*, 85, 8506-8510.) using the PolyATract mRNA Isolation System (Promega, Madison, Wis.) according to the manufacturer's instructions. Double stranded cDNA was synthesized, digested with Sau3AI and subjected to three cycles of RDA. The J2E erythroid cell line was used as driver to identify myeloid specific genes expressed in the lineage switched J2E-m2 target cell line.

The RDA procedure used was the same as previously published protocols (Hubank, M. and Schatz, D. G. (1994) Identifying differences in mRNA expression by representational difference analysis of cDNA. *Nucleic Acids Res*, 22, 5640-5648), except R-Bgl adaptors were not removed from driver cDNA prior to subtraction and the final difference product (DP3) was amplified for 35 cycles without mung bean nuclease treatment. In test PCR reactions, it was found that sufficient driver remained following extensive digestion to be readily amplified by PCR using the R-Bgl-24 oligonucleotide. In addition, R-ligated cDNA could not be amplified using either the J-Bgl-24 or N-Bgl-24 oligonucleotides (data not shown). Therefore, it was concluded that, removal of linkers was an unnecessary step, adding both to the time and cost of performing the procedure, while not providing significant benefits.

Oligonucleotide adaptor sequences used in these experiments were

```
                                  (SEQ ID NO: 9)
R-Bgl-12,   5'-GATCTGCGGTGA-3';

(SEQ ID NO: 10)
R-Bgl-24,   5'-AGCACTCTCCAGCCTCTCACCGCA-3';

(SEQ ID NO: 11)
J-Bgl-12,   5'-GATCTGTTCATG-3';

(SEQ ID NO: 12)
J-Bgl-24,   ACCGACGTCGACTATCCATGAACA-3';

(SEQ ID NO: 13)
N-Bgl-12,   GATCTTCCCTCG-3';

(SEQ ID NO: 14)
N-Bgl-24,   AGGCAACTGTGCTATCCGAGGGAA-3'.
```

Figure 1:
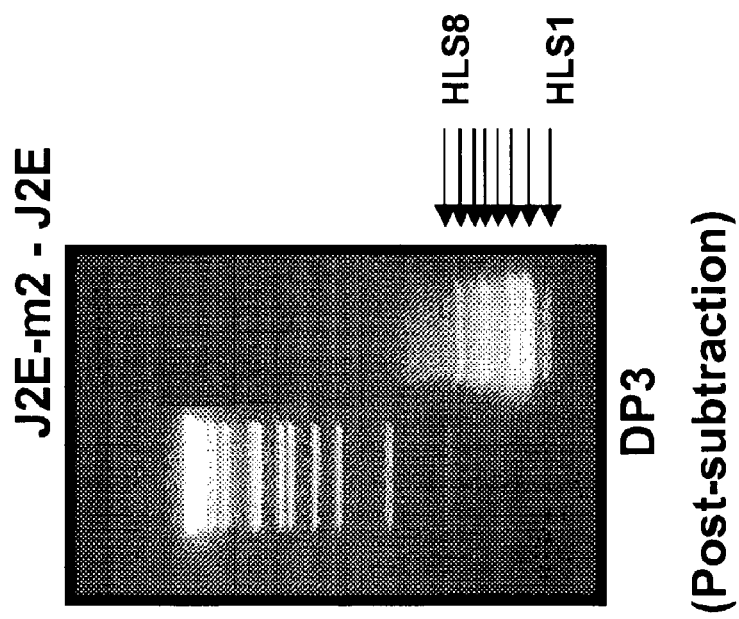
FIG. 1 illustrates cDNA Representational Difference Analysis. Ethidium bromide stained agarose gels demonstrating the appearance of PCR amplified representations from J2E driver and J2E-m2 target mRNA prior to RDA procedure (left panel) and J2E-m2 target cDNA following three rounds of the RDA procedure (DP3; right panel). The appearance of the sample changed from a uniform smear of approximately 0.2-1.5 kbp to being comprised mainly of eight discrete bands in DP3. These bands were labeled haemopoetic lineage switch (HLS) 1-8 and were isolated and sub-cloned for further analysis
Figure 1:
Figure 1:
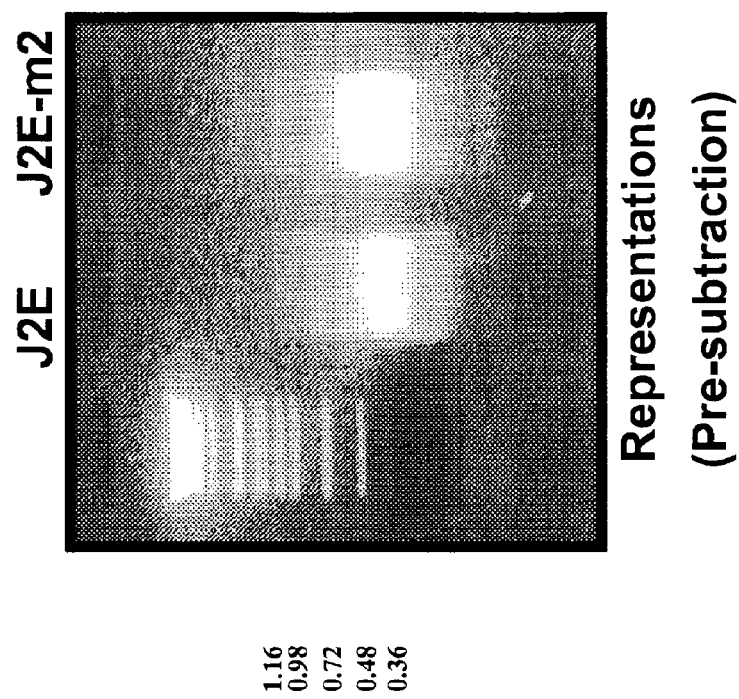

As shown in FIG. 1, the appearance of PCR amplified cDNA changed from a uniform smear in the starting representation, to eight discrete bands in the amplified third difference product (DP3). These bands were isolated, labelled hemopoietic lineage switch (HLS) 1-8 and sub-cloned for further analysis. Fragments enriched by this procedure were subcloned into pGEM-T (Promega) for further analysis. The identities of the 8 fragments are summarised in FIG. 2.

Two of the fragments isolated, HLS1 and HLS6, represented previously characterised myeloid specific genes cyclooxygenase 2 and GDP-dissociation inhibitor-D4, respectively, and validated the approach adopted for isolating myeloid specific genes (Adra et al., (1993) Identification of a novel protein with GDP dissociation inhibitor activity for the ras-like proteins CDC42Hs and rac I. *Genes Chromosomes Cancer*, 8, 253-261; DeWitt, D. L., el-Harith, E. A., Kraemer, S. A., Andrews, M. J., Yao, E. F., Armstrong, R. L. and Smith, W. L. (1990) The aspirin and heme-binding sites of ovine and murine prostaglandin endoperoxide synthases. *J Biol Chem*, 265, 5192-5198). HLS7 is the murine homologue of myeloid leukemia factor (MLF) 1 (Williams, J. H., Daly, L. N., Ingley, E., Beaumont, J. G., Tilbrook, P. A., Lalonde, J. P., Stillitano, J. P. and Klinken, S. P. (1999) HLS7, a hemopoietic lineage switch gene homologous to the leukemia-inducing gene MLF1. *Embo J*, 18, 5559-5566). HLS2 is the murine homologue of a glutamate carboxypeptidase. The remaining molecules represent two previously characterised, and ubiquitously expressed, molecules. HLS-5 that is described herein is a new member of the RBCC family of transcriptional regulators.

Sequence Analysis of HLS-5

Since HLS-5 represented a novel cDNA species that was induced during an erythroid to myeloid lineage switch, and therefore potentially played a role in the regulation of haemopoietic lineage determination, A mouse lymphohematopoietic progenitor cell line EML C.115 (Tsai, S., Bartelmez, S., Sitnicka, E. and Collins, S. (1994) Lymphohematopoietic progenitors immortalized by a retroviral vector harboring a dominant-negative retinoic acid receptor can recapitulate lymphoid, myeloid, and erythroid development. *Genes Dev*, 8, 2831-2841) library was screened for full length HLS-5 using the 361 bp HLS-5 RDA fragment (SEQ ID NO: 5) as a probe. Positive phage were isolated, cDNA inserts excised and subcloned into pBlueScript (Stratagene, La Jolla, Calif.) for sequencing using standard protocols.

To confirm that the complete 5'-end of the cDNA had been isolated, a rapid analysis of cDNA ends (RACE) strategy was adopted. The combined approaches resulted in a cDNA of 3,648 bp in length (SEQ ID 1) that contained a predicted open reading of 516 amino acids (SEQ ID 2). The 516 amino acid sequence has a methionine at both position 1 and position 16, either of which may potentially be the initiator methionine.

Searches of the DNA and Protein databases (Genbank (NIH) and Entrez (NCBI)) using the BLAST and FASTA programs revealed the predicted protein to have significant homology to several members of the ring finger, B-box, coiled-coil (RBCC) family of proteins. The highest similarity was with the ret finger protein (rfp) (Isomura, T., Tamiya-Koizumi, K., Suzuki, M., Yoshida, S., Taniguchi, M., Matsuyama, M., Ishigaki, T., Sakuma, S, and Takahashi, M. (1992) RFP is a DNA binding protein associated with the nuclear matrix. *Nucleic Acids Res,* 20, 5305-5310), acid finger protein (afp) (Chu et al., (1995) Cloning of a new "finger" protein gene (ZNF173) within the class I region of the human MHC. *Genomics,* 29, 229-239) and the recently identified hemopoietic ring finger 1 (HERF1) protein (Harada, H., Harada, Y., O'Brien, D. P., Rice, D. S., Naeve, C. W. and Downing, J. R. (1999) HERF1, a novel hematopoiesis-specific RING finger protein, is required for terminal differentiation of erythroid cells. *Mol Cell Biol,* 19, 3808-3815.) as these molecules have a single B-box domain. HLS-5 also had similarities to the promyelocytic leukaemia (PML) gene (de The et al., (1990) The t(15;17) translocation of acute promyelocytic leukaemia fuses the retinoic acid receptor alpha gene to a novel transcribed locus. Nature, 347, 558-561) gene and transcription intermediary factor (TIF) 1α which (Miki, T., Fleming, T. P., Crescenzi, M., Molloy, C. J., Blam, S. B., Reynolds, S. H. and Aaronson, S. A. (1991) Development of a highly efficient expression cDNA cloning system: application to oncogene isolation. *Proc Natl Acad Sci USA,* 88, 5167-5171)□, which share a similar structure except they have two B-box domains.

Using the Simple Modular Architecture Research Tool (SMART) (Schultz, J., Milpetz, F., Bork, P. and Ponting, C. P. (1998) SMART, a simple modular architecture research tool: identification of signaling domains. *Proc Natl Acad Sci USA,* 95, 5857-5864) HLS-5 was found to have conserved SPRY domain in the C-terminal half of the protein. The function of this domain is as yet unknown, however its presence in several apparently disparate families of proteins, including RBCC and some SOCS family members, suggest it may be important in a regulatory capacity.

To isolate the human homologue of HLS-5, a human foetal liver cDNA library (Clontech) was screened with a murine HLS-5 probe and subsequently progressively 5'-human HLS5 probes. The library screening resulted in a nucleotide sequence as shown in SEQ. ID NO 3, which had 81% identity to the murine cDNA. The murine cDNA was longer at the 5'-end, which includes the first of the two possible predicted initiating methionines and suggests that 12 bp of the human coding region (which may encode 4 amino acids at the N-terminus of the protein) are missing in addition to a portion of the 5'-untranslated region. The predicted human amino acid sequence (SEQ. ID NO 4) is 80.6% identical and 89.8% homologous to the murine sequence. The 5' end of the human sequence has been obtained subsequently and confirms that there is an additional possible initiator methionine at the beginning of an additional 4 amino acids at the N-terminus of the protein of SEQ ID NO: 4. The amino acid sequence of the human sequence starting at the second of the two possible methionines is shown as SEQ ID NO: 8. The corresponding nucleotide sequence which includes a 5' untranslated region is shown as SEQ ID NO: 7.

Analysis of HLS-5

Various region of the coding region of murine HLS-5 (bases 61-1573; bases 61-847 (RBCC domain); and, bases 1100-1573 (SPRY domain)) of SEQ ID NO 1 were subcloned in frame with the six-histidine residues of the pET expression system (Novagen, Madison, Wis.). Recombinant protein was expressed in *E. coli* using and affinity purified on Ni-NTA Agarose according to the manufacturers instructions (QIAGEN, Victoria, Australia). Two New Zealand White rabbits were immunized with 200 micrograms of recombinant protein three times at 4 week intervals and the resultant antisera was tested for specificity by Western blotting of recombinant protein, protein lysates from COS cells transiently transfected with HLS-5 and lysates from specific haemopoietic cell lines.

COS cell transfections: COS7 cells were transiently transfected with either the pEGFP vector alone or with the pEGFP-HLS5 (RBCC) vector (containing the RBCC domain (bases 61-847 of SEQ. ID NO 1) subcloned in frame with the GFP coding sequence) using the DEAE-dextran method as described elsewhere (Lowe, D. G. and Goeddel, D. V. (1987) Heterologous expression and characterization of the human R-ras gene product. *Mol Cell Biol,* 7, 2845-2856). Protein lysates were prepared using previously described methods (Tilbrook, P. A., Ingley, E., Williams, J. H., Hibbs, M. L. and Klinken, S. P. (1997) Lyn tyrosine kinase is essential for erythropoietin-induced differentiation of J2E erythroid cells. *Embo J,* 16, 1610-1619).

Immunoblotting: For detection of HLS-5, cell lysates (100 micrograms) were separated by SDS-PAGE, transferred to nitrocellulose membranes and analysed by immunoblotting with anti-HLS-5, anti-RBCC or anti-SPRY polyclonal antibodies raised as described above followed by horseradish peroxidase-conjugated secondary antibodies. Visualization was by enhanced chemiluminescence (Amersham, Bucks, UK).

Figure 6:
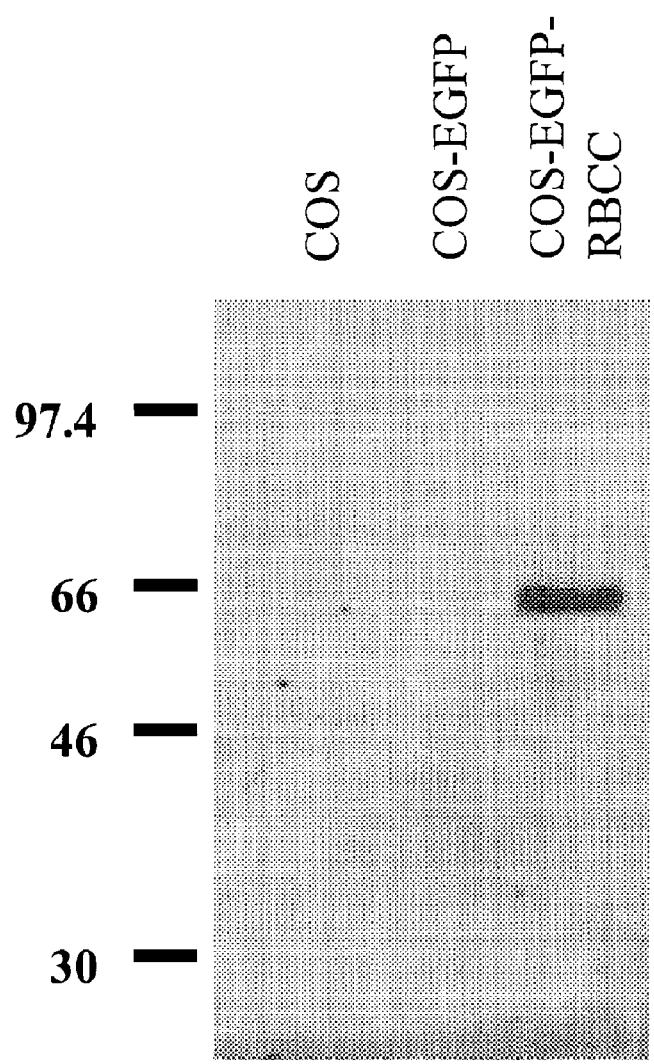
FIG. 6 illustrates western blot of COS cell lysates expressing GFP-HLS-5 (RBCC domain) with anti-RBCC Ab. To test the specificity of the anti-RBCC antibody, lysates (200 μg) from un-transfected COS cells, COS cells transiently transfected with the pEGFP-c2 plasmid (which expressed the Green Fluorescent Protein) or COS cells transfected with the pEGFP-HLS5 (RBCC) plasmid (which expresses the RBCC fragment of HLS5 fused to GFP) were separated by PAGE transferred to nitrocellulose and immunoblotted with the anti-RBCC polyclonal antibody and a horse radish-peroxidase secondary antibody. Blots were developed by Enhanced Chemiluminescence. The anti-RBCC serum specifically recognises the GFP-RBCC fusion protein.
Figure 7:
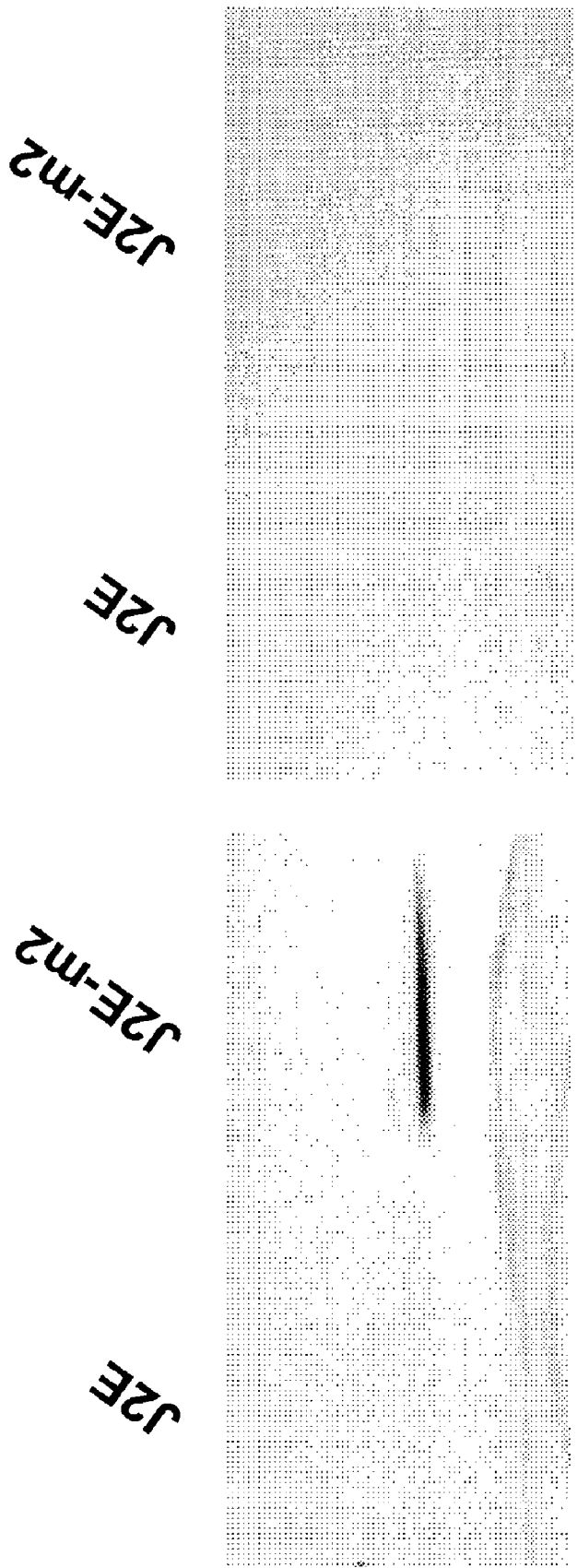
FIG. 7 illustrates western blot of J2E and J2E-m2 lysates with anti-RBCC Ab. J2E and J2E-m2 lysates (400 were separated by PAGE, transferred to nitrocellulose and immunoblotted with either the anti-RBCC polyclonal serum or pre-immune serum. A specific 58 kDa protein was detected only by the anti-RBCC serum in J2E-m2 lysate. The size of this band agrees with the calculated molecular weight of the predicted HLS-5 open reading frame (58.7 kDa) and the expression pattern agrees with the Northern blot analysis.
Figure 8:
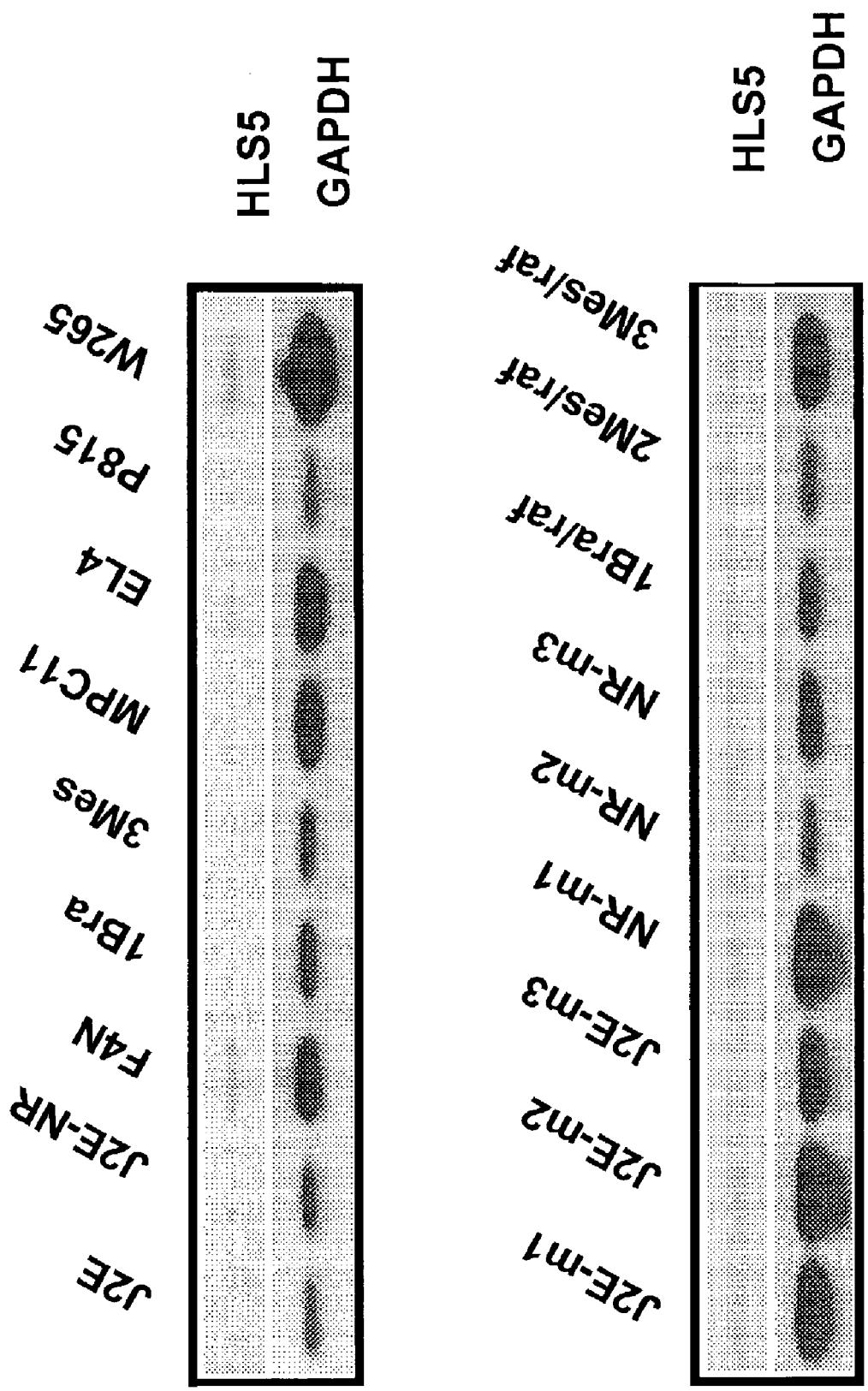
FIG. 8 illustrates northern blot of haemopoietic cell lines. mRNA from the indicated murine cell lines was probed with [$^{32}$P]-labeled HLS5. HLS5 was expressed by all myeloid lines tested (W265, J2E-m1, J2E-m2, J2E-m3, NR-m1, NR-m2, NR-m3, 1 Bra/raf, 2Mes/raf and 3 Mes/raf), the F4N erythroleukaemic line and the EL4 T-cell line. No expression was detected in J2E or J2E-NR erythroid lines, the 1 Bra, 3Mes or MPC11 B-cell lines or the P815 mast cell lines. GAPDH serves as a loading control.

Results: As shown in FIG. 6, the anti-RBCC antisera recognised a specific 61 kDa band in COS cells transfected with a construct expressing a green fluorescent protein (GFP)-RBCC fusion protein. As expected, the pre-immune sera did not recognise this protein. Furthermore, the anti-RBCC and FL serum recognised a specific 62 kDa band in J2E-m2 cells that was not present in the parental erythroid J2E line which confirms the differential expression of the gene and further demonstrated the specificity of the reagent (FIG. 7).

Pattern of HLS-5 Gene Expression

Figure 3:
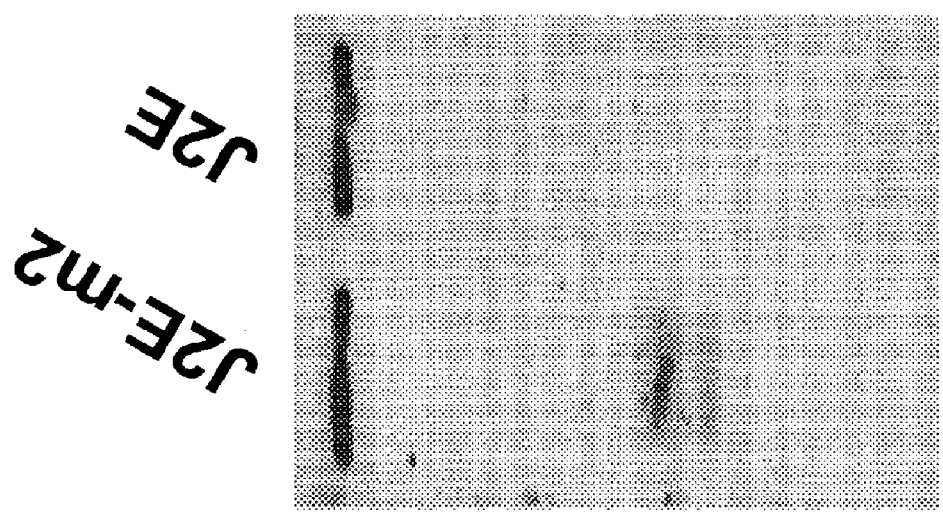
FIG. 3 illustrates HLS-5 Southern blot of Representations. J2E and J2E-m2 representations (1 μg) were separated by agarose gel electrophoresis and transferred to nylon membrane using standard protocols. The membrane was then hybridised with a [$^{32}$P]-labeled HLS5 probe. Following high stringency washes, the membrane was exposed to autoradiography film to determine differential expression of HLS5 in the representations.
Figure 4:
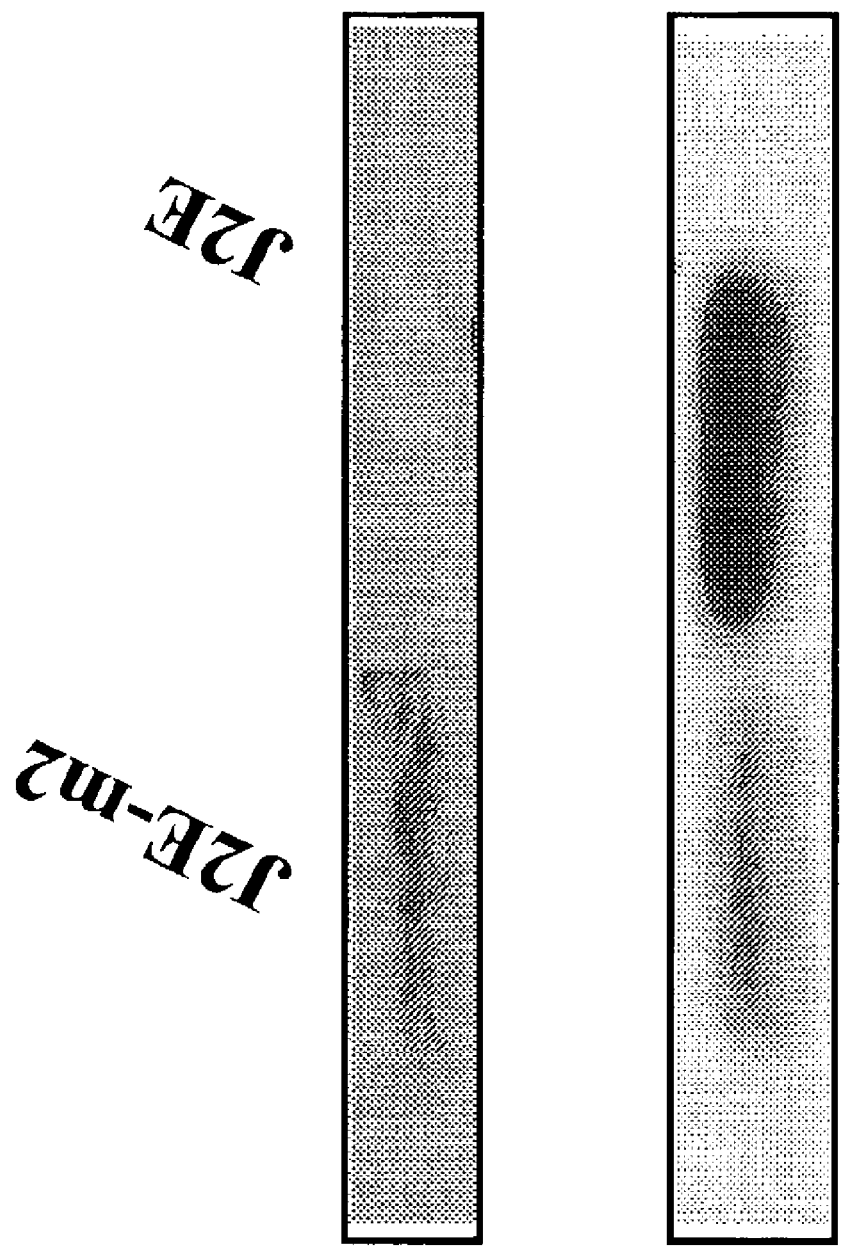
FIG. 4 illustrates northern Analysis (J2E/J2E-m2 mRNA). mRNA (1 μg) from J2E and J2E-m2 cells was separated on a formaldehyde agarose gel and transferred to nylon membranes using standard protocols. The membrane was then probed with a [$^{32}$P]-labelled HLS5 probe, washed and exposed to autoradiography film. To demonstrate that there was in fact mRNA in the J2E lane, a [$^{32}$P]-labelled glyceraldehyde-3-phosphate dehydrogenase (GAPDH) probe was subsequently hybridised to the membrane. This result confirms that HLS5 is expressed by J2E-m2 cells and not J2E cells.
Figure 5:
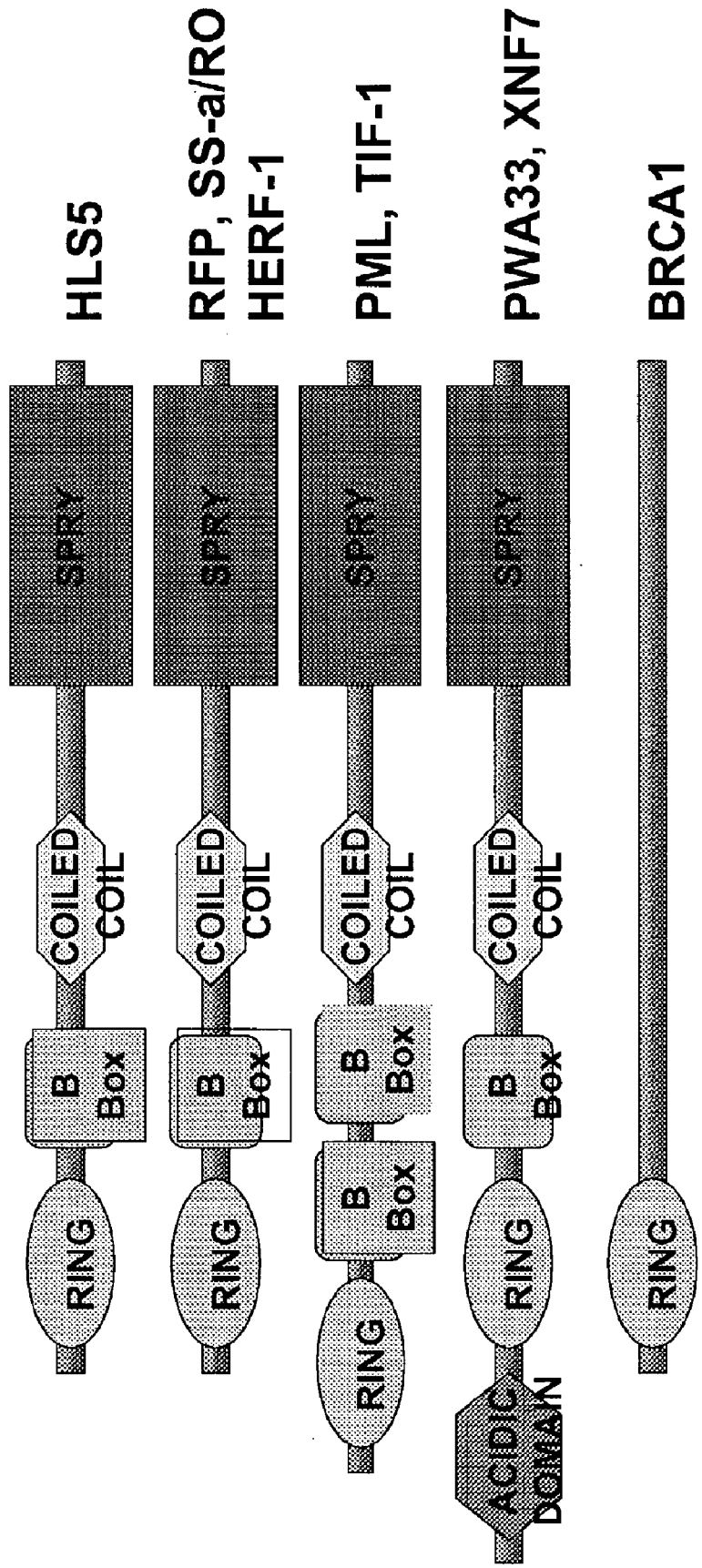
FIG. 5 illustrates HLS-5 homologs. Diagrammatic representation of HLS5 protein structure and comparison to other related proteins. Protein domains were identified using the Simple Modular Architecture Research Tool (SMART) (Schultz et al (1998) *PNAS* 95:5857-5864) and homologs were identified using a Blast search of the protein databases.

To investigate the differential expression pattern of HLS-5, Southern and Northern blot analysis of starting representations as well as J2E and J2E-m2 poly(A)+ RNA was performed using standard techniques using standard techniques (Sambrook et al) and 361 bp fragment (SEQ ID NO 5) as probe. Only the myeloid representation and mRNA expressed HLS-5 (FIGS. 3 and 4).

Figure 9:
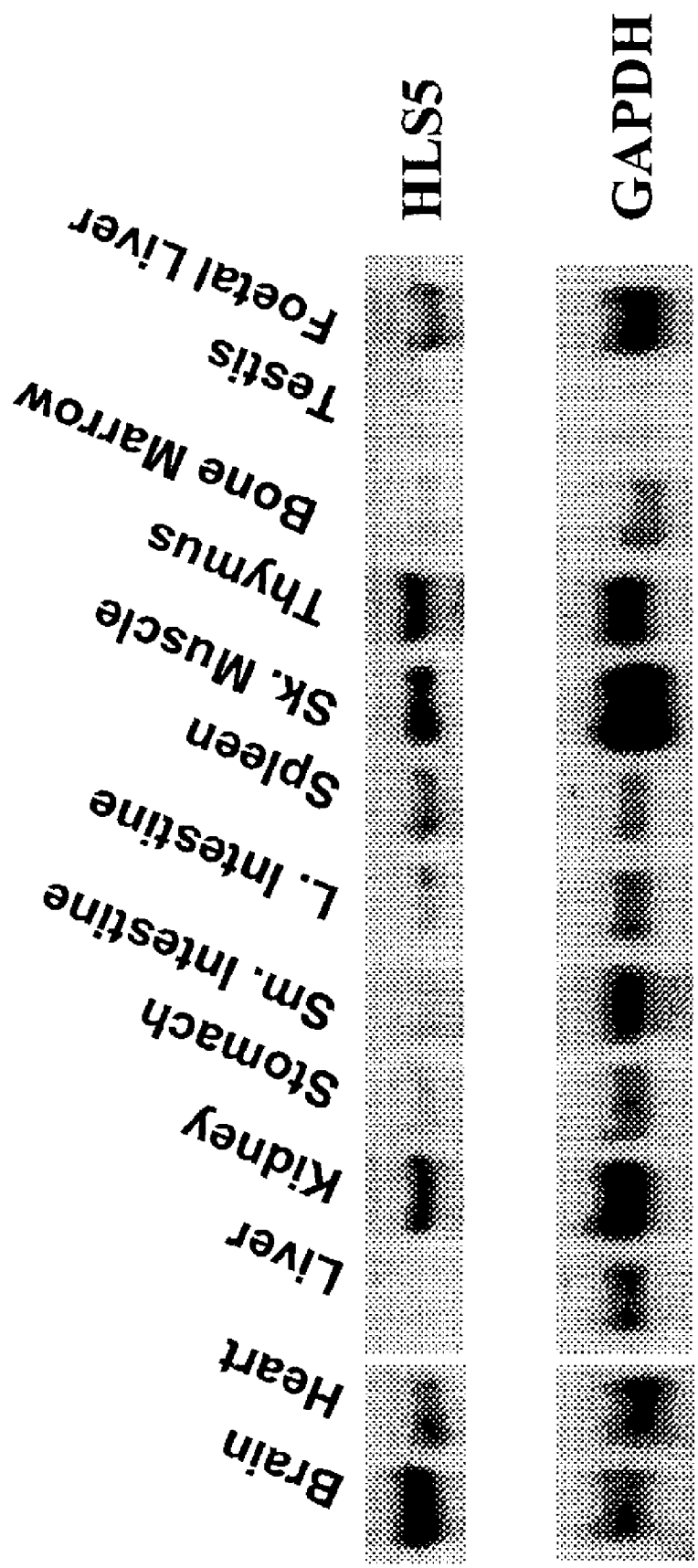
FIG. 9 illustrates northern blot of murine tissue RNA. RNA from the indicated murine tissues was probed with [$^{32}$P]-labelled HLS5. HLS5 was expressed by all tissues tested with the exception of adult liver. GAPDH serves as a loading control.

Northern blot analysis was used as an initial approach to further define the expression pattern of HLS-5. Analysis of a panel of haemopoietic cell lines revealed that HLS-5 was expressed principally by myeloid cell lines, although some expression was seen in the F4N murine erythroleukemic (MEL) cell line and the EL4 T-cell line (FIG. 9). Expression of HLS-5 was not regulated during in vitro differentiation of murine M1 monoblastoid cells, MEL cells or 70Z/3 B-cells (data not shown). Out-with the hemopoietic system, however, hybridisation of mouse tissue RNA revealed that HLS-5 was widely expressed (FIG. 9). The most notable exception was the absence of expression in the adult liver, while liver from 12-day old mouse foetus' displayed weak HLS-5 expression. This observation is commensurate with a potential role for HLS-5 in haemopoiesis.

Figure 10:
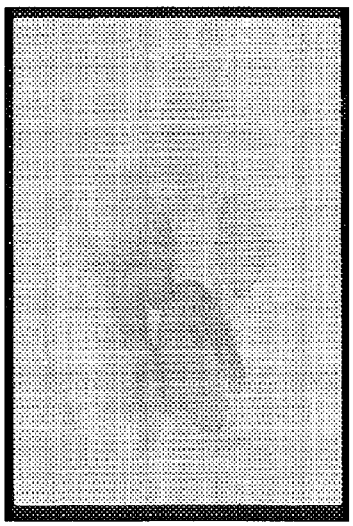
FIG. 10 illustrates whole mount in situ hybridisation.
Figure 10:
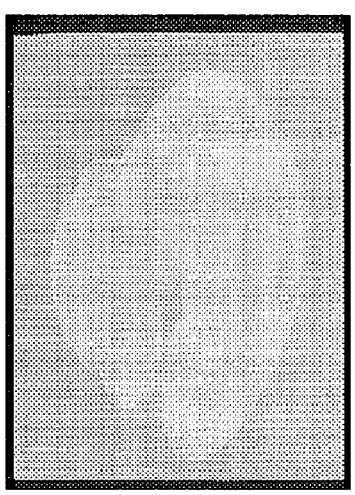
Figure 10:
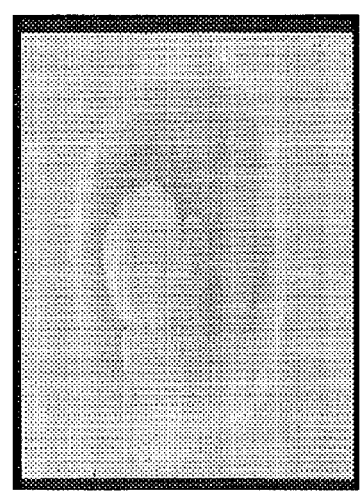
Figure 10:
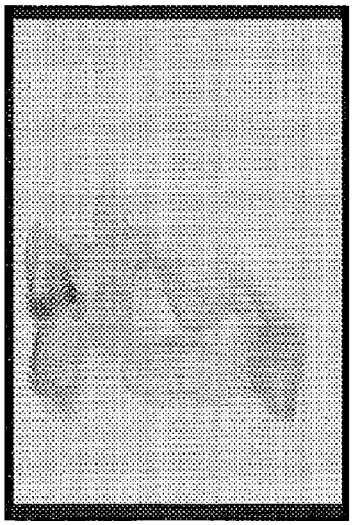
Figure 10:
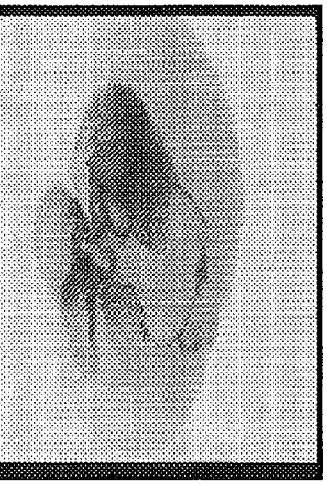

HLS-5 expression was also investigated during murine development by whole mount in situ hybridisation (FIG. 10). Highest expression was seen in the developing lung at day 10.5 of gestation. Strikingly, HLS-5 expression was also seen in the digital rays, neural crest, pericardial bulge and pharangeal arches which represent those regions of the developing embryo undergoing apoptosis. This expression pattern is reminiscent of T:G thymine DNA glycosylase.

Figure 13:
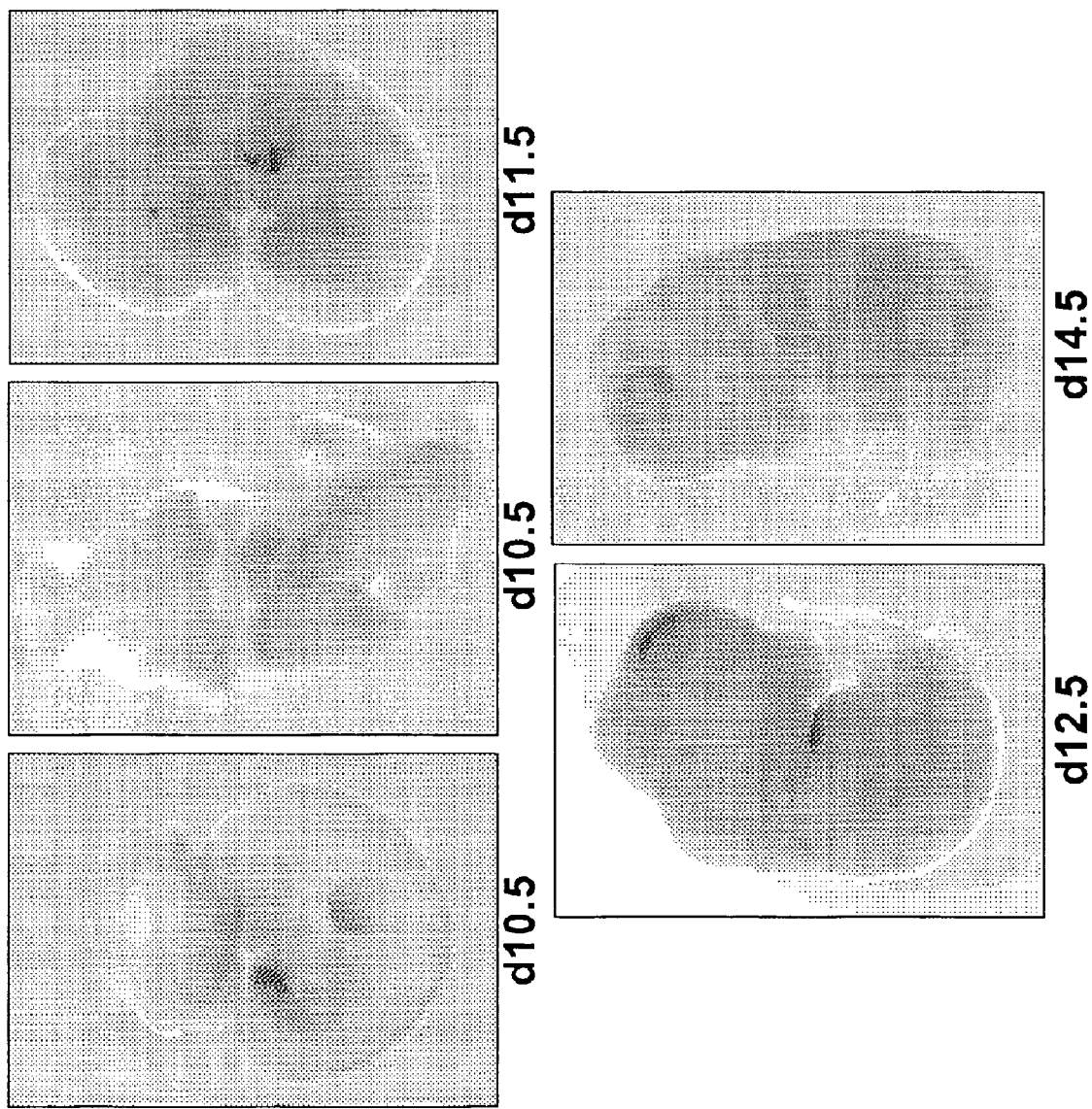
FIG. 13 illustrates whole mount in situ hybridisation of HLS5 expression during day 10.5 to day 14.5 of embryogenesis.

FIG. 13 illustrates whole mount in situ hybridisation of HLS5 expression during day 10.5 to day 14.5 of embryogenesis. These results shown that during embryo development, HLS5 is expressed in the brachial arches, limbs, neural tube, somites and dorsal root ganglion at day 10.5. Expression occurs in the eye between day 11.5 and 12.5. During later stages, the limb staining becomes more restricted to the interdigital regions and the skeletal staining is still evident.

Subcellular Localization of HLS-5

COS cells were transiently transfected with the pcDNA3-mHLS5-Myc plasmid (which expresses the full length murine HLS5 fused to a Myc-epitope tag and analysed by confocal microscopy. The results obtained show that HL5 localises to the cytoplasm, centrosome and has punctate nuclear staining (data not shown).

Chromosomal Localisation of HLS-5

A 2,358 bp fragment of human genomic DNA encoding part of the human HLS5 gene was generated by PCR using primers HLS-5-1 (GAAACACAAGGCCG AAAACGC SEQ ID NO: 15) and HLS-5-2 (AAGCCTGAGCGTGTAT-CATGGTAGCAGC SEQ ID NO:16). This fragment was nick-translated with biotin-14-dATP and hybridised in situ at a final concentration of 10 ng/ul to metaphases from two normal males. The fluorescence in situ hybridisation (FISH) method was modified from that previously described (Callen et al., (1990) Reassessment of two apparent deletions of chromosome 16p to an ins (11; 16) and at (1; 16) by chromosome painting. Ann Genet, 33, 219-221) in that chromosomes were stained before analysis with both propidium iodide (as counterstain) and DAPI (for chromosome identification). Images of metaphase preparations were captured by a cooled CCD camera using the ChromoScan image collection and enhancement system (Applied Imaging Int. Ltd.). FISH signals and the DAPI banding pattern were merged for figure preparation.

Figure 11:
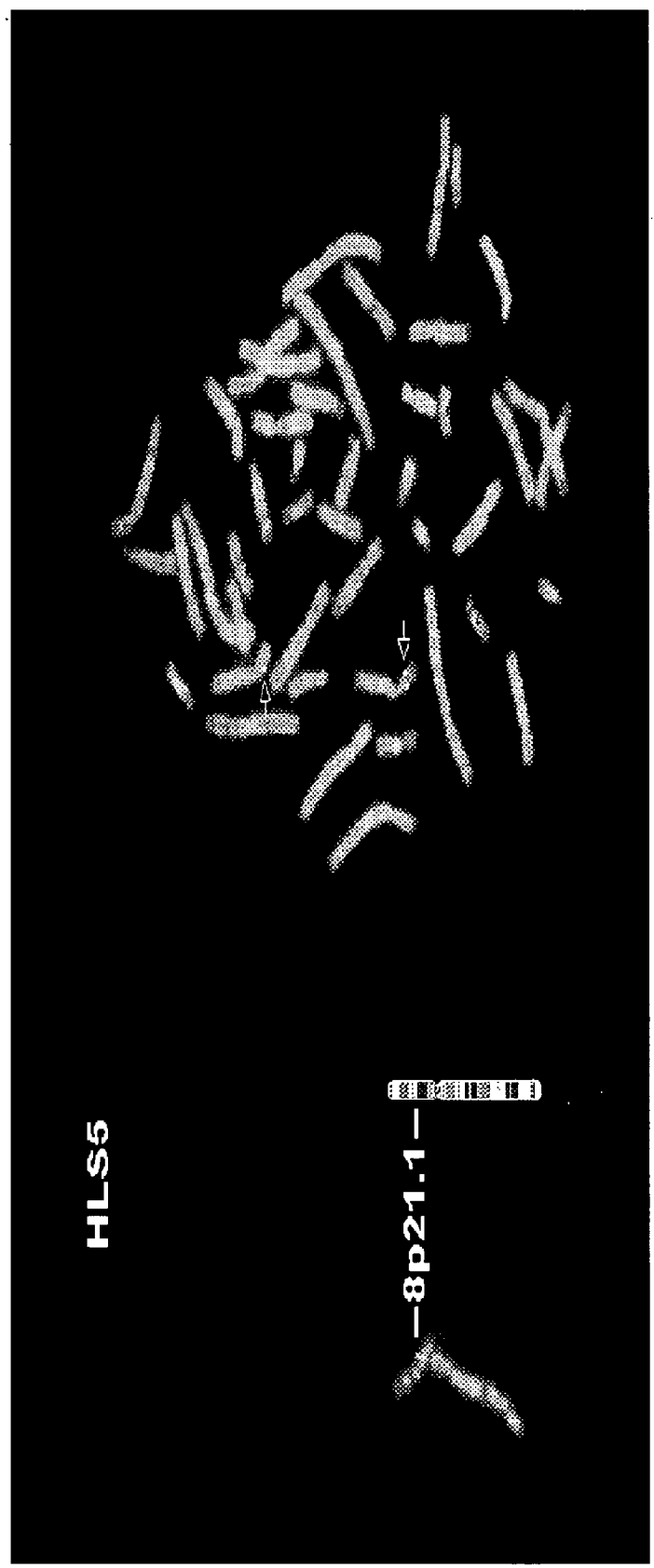
FIG. 11 illustrates fluorescent in situ hybridisation to determine chromosomal localisation of HLS-5 (representative example of analysis of 20 metaphases from a normal male). Each metaphase examined showed a signal on one or both chromatids of chromosome 8 in the proximal region of band 8p21. 15 metaphases from a second male gave similar results. The image shows a merged image of FISH signals and DAPI staining.
Figure 14:
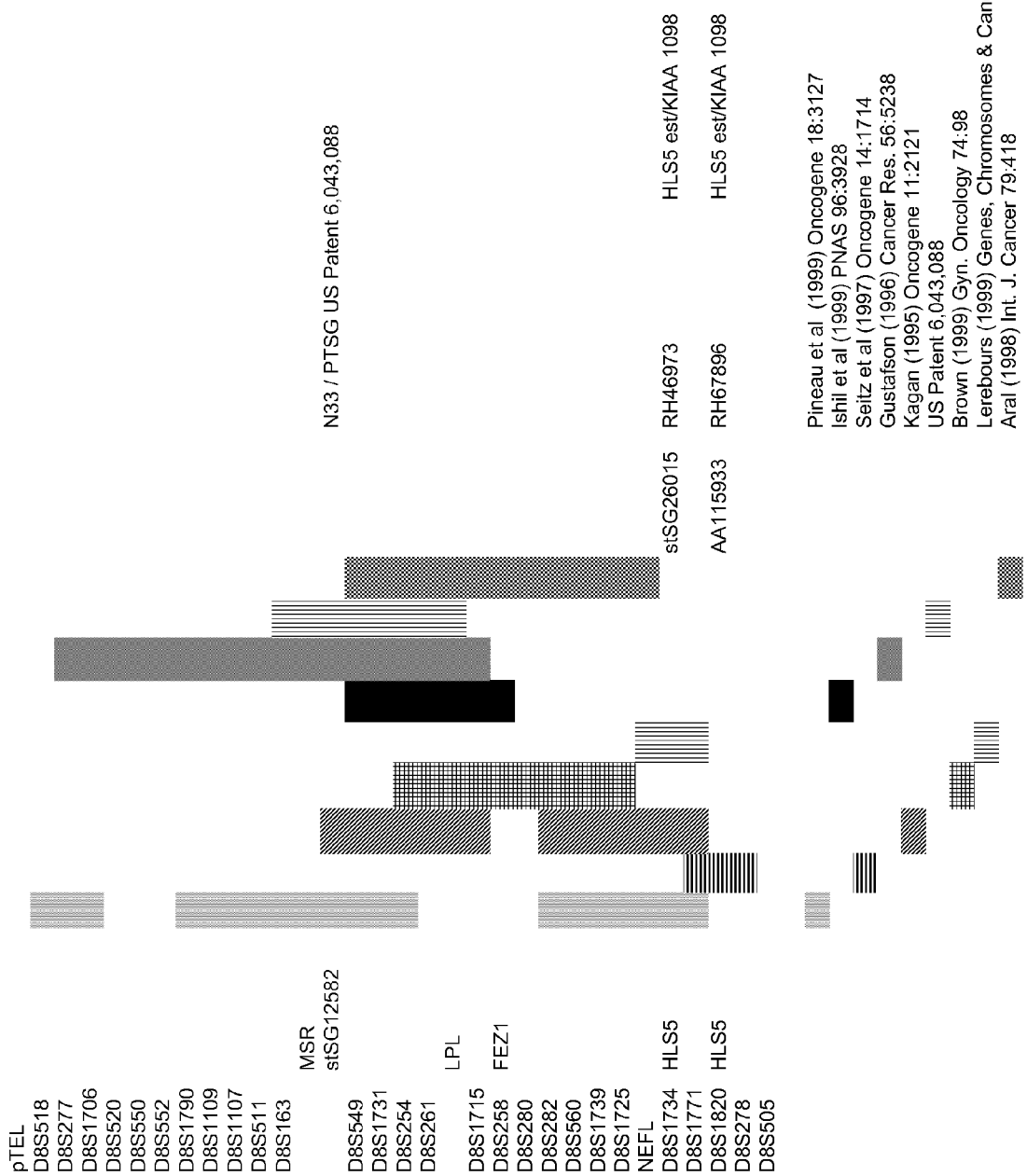
FIG. 14 illustrates the position of HLS5 on chromosome 8 in relation to a number of regions that have been shown to be deleted in a number of cancers.

A fragment of human HLS-5 isolated from a foetal liver cDNA library was used for fluorescent in situ hybridisation (FISH) of human metaphase spreads. FIG. 11 shows that HLS-5 localises to 8p21.1. In addition, FIG. 14 illustrates the position of HLS5 on chromosome 8 in relation to the location of a number of regions shown to be deleted in a number of cancers.

Identification of HLS-5 Interacting Proteins

Yeast two-hybrid analysis. The yeast two-hybrid procedures used were essentially as described by Vojtek et al. (1993), using the *S. cerevisiae* L40 strain (MATa, his3α200, trp1-901, leu2-3, 112, ade2, LYS2::(lexAop)$_4$-HIS3, URA3:: (lexAop)$_8$-lacZ, GAL4). Murine HLS-5 cDNA (bases 61-1573 of SEQ. ID NO 1) was subcloned into pBTM116 (Vojteck et al, 1993) to generate a LexA DNA binding domain-HLS-5 fusion. The L40 strain was transformed with pBTM116-HLS-5 and used as the "bait" in a two hybrid screen of a cDNA library in the VP16 transcriptional activation domain fusion plasmid (pVP16) made from mRNA derived from the lymphohematopoietic progenitor cell line EML C.115 (Tsai, S., Bartelmez, S., Sitnicka, E. and Collins, S. (1994) Lymphohematopoietic progenitors immortalized by a retroviral vector harboring a dominant-negative retinoic acid receptor can recapitulate lymphoid, myeloid, and erythroid development. *Genes Dev*, 8, 2831-2841). Transformants were plated onto HIS$^-$ plates to select for HIS3 reporter activation. Clones replated onto HIS$^-$ plates were then assayed for β-galactosidase (β-gal) activity using the filter assay. The pBTM116-HLS7 plasmid was then cured from the HIS3$^+$/β-gal$^+$ clones before transformation with pBTM116, pBTM1116-HLS-5 or pBTM116-lamin (expressing a LexA fusion of human lamin) and then assayed for HIS3 and β-gal activity. The pVP16 plasmids from the cured clones were then rescued into *E. coli* and sequenced. These plasmids were subsequently co-transformed with pBTM116-HLS-5 or pBTM116-lamin into the yeast L40 strain before performing HIS3 and β-gal assays.

Of the 257 potential HLS5 interacting proteins, 9 clones were initially sequenced. These can be classified in 4 groups: 1) an hCMV interacting protein, 2) mUBC9, 3) two different forms of T:G Thymine specific DNA glycosylase, and 4) the Human EST for HLS5 present in the GenBank database.

| Interacting clones | Accession #: |
|---|---|
| 1) hCMV interacting protein = | X97571 |
| | CAA66184 |
| 2) mUBC9 = | U76416 |
| | X99739 |
| | U94402 |
| | CAA68072 |
| 3) T:G thymine DNA glycosylase | AF069519 |
| | AAC31900 |
| 4) EST for human HLS5 (KIAA1098) | BAA83050 |
| | AB029021 |

Discussion

The identification of mUBC9 and T:G DNA glycosylase as proteins that interact with HLS-5 further support the idea that HLS-5 functions as part of the cell cycle machinery. UBC9 (ubiquitin conjugating enzyme 9) has been shown to play an essential role in cell cycle progression, especially at the G2/M boundary. In particular, UBC9 has been shown to be involved in the degradation of key nuclear proteins involved in cell cycle progression. Furthermore, UBC9 binds to and modulates the activity of ETS-1, a transcription factor that regulates cell growth, differentiation and apoptosis.

UBC9 also binds to molecules involved in DNA repair such as topoisomerase II and poly(ADP-ribose) polymerase (PARP). Consequently, since HLS-5 also interacts with T:G DNA glycosylase, a DNA repair enzyme that recognises thymine, guanine mismatches, it seems possible the HLS-5 is also involved in DNA repair pathways. Indeed there are a number of precedents for proteins that interact with both DNA repair proteins and cell cycle progression proteins since the two processes are interrelated.

Further yeast two-hybrid studies identified additional interacting proteins. These are shown below in Table 1. Of the 257 potential HLS5 interacting proteins, 72 clones have been sequenced thus far, resulting in 53 different molecules which interact with HLS5.

TABLE 1

| Yeast two hybrid interactors of HLS-5 | |
|---|---|
| CLONE | ACCESSION NO. |
| 28S ribosomal subunit | |
| 45S pre-rRNA | X82564 |

TABLE 1-continued

Yeast two hybrid interactors of HLS-5

| CLONE | ACCESSION NO. |
|---|---|
| Acly | NM_016987 |
| Actin | U39357 |
| Amphiphysin | NM_009668 |
| API-5 | U75285 |
| Capping protein isoform 1 | U10406 |
| Cezanne | AJ293573 |
| CGI-48 | NM_010239 |
| Chaperone subunit 5 (Cct) | NM 007637 |
| Complement 1qBP | AJ001101 |
| CTD, RNA pol II binding protein | U49057 |
| DAM1 | AF081788 |
| Def-6 | AJ276095 |
| DIPB | AJ249129 |
| EIF3 | U78525 |
| eIF4A1 | X03039 |
| Ferritin Heavy chain | NM_009668 |
| Ferritin light chain | J04716 |
| Flt3 interacting ZF protein (FIZ1) | AF126747 |
| FOG | AF006492 |
| hnRNP A/B | |
| hnRNP M4 | X72018 |
| KIAA0296 | AB002294 |
| KIAA1321 | AB037742 |
| Kinesin-related protein (KIFC5A) | AF221102 |
| LOC55954 | AL160311 |
| mGAPDH | |
| mGlutamate dehydrogenase | X57024 |
| mGRASP1 | AF274058 |
| mHLS5 | AF145374 |
| mLamin C | |
| mTIF4B | X55733 |
| mUBC9 | X99739 |
| Myosin Va (Myo5a) | NM 010864 |
| nCoA-62 | AF045184 |
| Novel clone (DNA helicase) | KIAA0224 |
| Novel clone (HMG Domain) | KIAA0306 |
| Novel, Chromosome 14 | AC007686 |
| NRBF-2 | AB024930 |
| Peregrin | AF176815 |
| Pigpen | AF224264 |
| Plectin | X59601 |
| Prot. Inhibit. Of Stat (PIAS1) | AF077950 |
| Rho GDP-dissociation factor | X69550 |
| ribosomal prot. L13/A52 | U2817 |
| T:G DNA Glycosylase | AF069519 |
| TAF2N | X98893 |
| Tim23 | AB021122 |
| Ubiquitin/60S fusion protein | AF118402 |
| UNC-2 | AF202723 |
| VDAC1 | AB0396621 |
| Vimentin | X56397 |

Testing Tumour Suppressor Activity of HLS-5

The tumor suppressor activity of HLS-5 is assessed in both in vitro cell culture conditions and in nude mouse animal models.

In Vitro Testing (Cell Lines)

Figure 12:
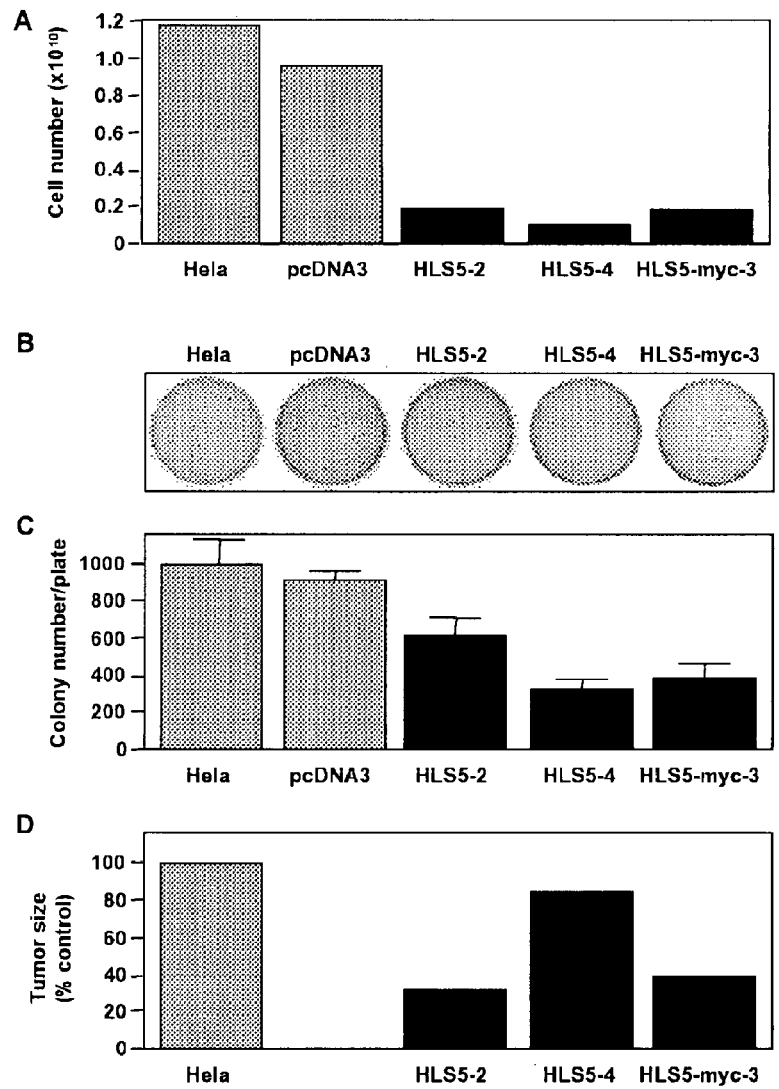
FIG. 12 illustrates the reduction of cell growth, colony and tumor formation following the introduction of HLS5 into HeLa cells.

To assess the effect of HLS5 expression on cell clonogenicity, tumour cell lines are tested for the ability to grow in soft agar. Typically, approximately $10^3$-$10^4$ cells are plated into soft agar. Colonies were counted after 21 days in culture. FIG. 12 illustrates the reduction of cell growth, colony and tumor formation following the introduction of HLS5 into HeLa cells. Panel A: $5\times10^5$ cells were cultured and maintained in log phase for 18 days and counted. Panels B, C.: Cells ($5\times10^3$) were plated into soft agar and colonies (B) were counted after 21 days in culture to access clonogenicity (C). HLS5-2, HLS5-4 and HLS5-myc-3 are three different HLS5 clones. pcDNA3 is vector alone. Hela is no vector.

Ex Vivo Gene Therapy.

To assess the effect of HLS-5 expression on tumorigenicity, tumour cell lines are tested for their ability to produce tumours in nude mouse models. Approximately $2\times10^7$ cells are plated into flasks, and cells are treated with sucrose buffer containing control vector or HLS-5 vector. Following overnight infections, cells are harvested and approximately $10^7$ cells are injected subcutaneously into the left and right flanks of BALB/c nude mice (4/group). One flank is injected with control vector treated cells, while the contralateral flank is injected with HLS-5 vector treated cells, each mouse serving as its own control. Animals receiving bilateral injections of untreated cells serve as an additional control for tumour growth. Tumour dimensions (length, width, height) and body weights are then measured twice per week. Tumour volumes are estimated for each animal assuming a spherical geometry with radius equal to one-half the average of the measured tumour dimensions.

FIG. 12, panel D illustrates the results obtained when cells ($10^6$) were injected intradermally into four sites of five ARC nude mice and the size of tumors formed measured after seven days. The average tumor size is shown with HeLa cell tumors equal to 100%.

Discussion

To test the tumor suppressor activity of HLS5 in vitro and in a nude mouse model, HLS5 was expressed ectopically in HeLa cells. The rate of cell growth was reduced, as was the ability of the cells to form colonies in soft agar. In addition, the ability of the cells to form tumors in nude mice was reduced.

In Vivo Tumour Suppression with HLS-5.

Cancer cell lines are injected subcutaneously into female BALB/c athymic nude mice. Tumours are allowed to develop for 32 days. At this point, a single injection of either control vector or HLS-5 vector is injected into the peritumoral space surrounding the tumour. Tumours are then excised at either Day 2 or Day 7 following the injection, and poly-A+ RNA is isolated from each tumour. Reverse transcriptase-PCR using HLS-5 specific primers, are then used to detect HLS-5 RNA in the treated tumours. Amplification with actin primers serves as a control for the RT-PCR reaction while a plasmid containing the recombinant-(HLS-5) sequence will serve as a positive control of the recombinant-(HLS-5) specific band.

In a separate experiment, cells are injected into the subcutaneous space on the right flank of mice, and tumours are allowed to grow for 2 weeks. Mice receive peritumoral injections of buffer or recombinant vector twice weekly for a total of 8 doses. Tumour growth is monitored throughout treatment in the control animals receiving control vector and buffer and those animals receiving HLS-5 vector. Body weight and survival time is also monitored.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of reducing cancer cell growth, the method comprising the steps of:
   (a) administering to said cancer cells an HLS-5 molecule selected from the group consisting of:
      (i) polynucleotides comprising the nucleotide sequence set out in SEQ ID NO:1 or SEQ ID NO:3;
      (ii) polynucleotides encoding an HLS-5 polypeptide comprising at least 95% sequence identity with the sequence set out in SEQ ID NO:2 or SEQ ID NO:4; and
      (iii) an HLS-5 polypeptide comprising at least 95% sequence identity with the sequence set out in SEQ ID NO:2 or SEQ ID NO:4
   wherein said HLS-5 molecule is administered in an amount effective to reduce growth of said cancer cells.

2. The method of claim 1, wherein said cancer cells have aberrant growth.

3. The method of claim 1, wherein said HLS-5 polynucleotide is contained in a vector.

4. The method of claim 1, wherein the cancer cells are breast cancer cells.

5. The method of claim 1, wherein the cancer cells are leukemia cells.

6. The method of claim 1, wherein the cancer cells are prostate cancer cells.

7. The method of claim 1, wherein the cancer cells are ovarian cancer cells.

8. The method of claim 1, wherein the HLS-5 molecule is a polynucleotide comprising the nucleotide sequence set out in SEQ ID NO:1.

9. The method of claim 1, wherein the HLS-5 molecule is a polynucleotide comprising the nucleotide sequence set out in SEQ ID NO:3.

10. The method of claim 1, wherein the HLS-5 molecule is a polynucleotide encoding an HLS-5 polypeptide comprising at least 95% sequence identity with the sequence set out in SEQ ID NO:2.

11. The method of claim 1, wherein the HLS-5 molecule is a polynucleotide encoding an HLS-5 polypeptide comprising at least 95% sequence identity with the sequence set out in SEQ ID NO:4.

12. The method of claim 1, wherein the HLS-5 molecule is a polypeptide comprising at least 95% sequence identity with the sequence set out in SEQ ID NO:2.

13. The method of claim 1, wherein the HLS-5 molecule is a polypeptide comprising at least 95% sequence identity with the sequence set out in SEQ ID NO: 4.

* * * * *